(12) United States Patent
Flanigan et al.

(10) Patent No.: US 9,862,945 B2
(45) Date of Patent: Jan. 9, 2018

(54) RECOMBINANT ADENO-ASSOCIATED VIRUS DELIVERY OF EXON 2-TARGETED U7SNRNA POLYNUCLEOTIDE CONSTRUCTS

(71) Applicant: RESEARCH INSTITUTE AT NATIONWIDE CHILDREN'S HOSPITAL, Columbus, OH (US)

(72) Inventors: Kevin Flanigan, Columbus, OH (US); Adeline Vulin-Chaffiol, Columbus, OH (US); Nicolas Wein, Columbus, OH (US)

(73) Assignee: RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 0 days.

(21) Appl. No.: 14/785,769

(22) PCT Filed: Apr. 18, 2014

(86) PCT No.: PCT/US2014/034702
§ 371 (c)(1),
(2) Date: Oct. 20, 2015

(87) PCT Pub. No.: WO2014/172669
PCT Pub. Date: Oct. 23, 2014

(65) Prior Publication Data
US 2016/0076028 A1   Mar. 17, 2016

Related U.S. Application Data

(60) Provisional application No. 61/814,256, filed on Apr. 20, 2013.

(51) Int. Cl.
| | | |
|---|---|---|
| C07H 21/02 | (2006.01) | |
| A61K 48/00 | (2006.01) | |
| C12N 15/113 | (2010.01) | |
| C07K 14/47 | (2006.01) | |
| C12N 15/86 | (2006.01) | |
| C12N 15/11 | (2006.01) | |
| C12N 7/00 | (2006.01) | |
| A01K 67/00 | (2006.01) | |

(52) U.S. Cl.
CPC .......... *C12N 15/113* (2013.01); *A61K 48/005* (2013.01); *C07K 14/4708* (2013.01); *C12N 7/00* (2013.01); *C12N 15/111* (2013.01); *C12N 15/86* (2013.01); *C12N 2310/11* (2013.01); *C12N 2320/32* (2013.01); *C12N 2320/33* (2013.01); *C12N 2330/51* (2013.01); *C12N 2750/14132* (2013.01); *C12N 2750/14143* (2013.01); *C12N 2750/14171* (2013.01); *C12N 2750/14321* (2013.01); *C12N 2750/14333* (2013.01)

(58) Field of Classification Search
CPC .................. C12N 15/113; C12N 15/86; C12N 2750/14132; C12N 2750/14143; C12N 2750/14171; A61K 48/005
See application file for complete search history.

(56) References Cited

U.S. PATENT DOCUMENTS

| | | | |
|---|---|---|---|
| 5,173,414 A | 12/1992 | Lebkowski et al. | |
| 5,658,776 A | 8/1997 | Flotte et al. | |
| 5,786,211 A | 7/1998 | Johnson | |
| 5,871,982 A | 2/1999 | Wilson et al. | |
| 6,258,595 B1 | 7/2001 | Gao et al. | |
| 6,566,118 B1 | 5/2003 | Atkinson et al. | |
| 7,282,199 B2 | 10/2007 | Gao et al. | |
| 7,790,449 B2 | 9/2010 | Gao et al. | |
| 2006/0099616 A1* | 5/2006 | van Ommen ...... | A61K 48/0016 435/6.11 |
| 2012/0077860 A1 | 3/2012 | Garcia | |
| 2013/0045538 A1 | 2/2013 | Garcia et al. | |
| 2013/0072541 A1 | 3/2013 | Garcia | |

FOREIGN PATENT DOCUMENTS

| | | |
|---|---|---|
| WO | WO-1995/13365 A1 | 5/1995 |
| WO | WO-1995/13392 A1 | 5/1995 |
| WO | WO-1996/17947 A1 | 6/1996 |
| WO | WO-1997/06243 A1 | 2/1997 |
| WO | WO-1997/09441 A2 | 3/1997 |
| WO | WO-199708298 A1 | 3/1997 |
| WO | WO-1997/21825 A1 | 6/1997 |
| WO | WO-1998/09657 A2 | 3/1998 |
| WO | WO-1999/11764 A2 | 3/1999 |
| WO | WO-2001/83692 | 11/2001 |
| WO | WO 2011/078797 A2 * | 6/2011 |

OTHER PUBLICATIONS

Aartsma-rus et al: Antisense-induced exon skipping for duplications in Duchenne muscular dystrophy, *BMC Medical Genetics*, 8(1):43 (2007).
Alencastro et al., Targeted Exon Skipping to Correct Duplicated Exons in the Dystrophin Gene, 8th Australasian Gene Therapy Society Meeting, *J. Gene Med.*, 332 (2013).
Biggar et al., Deflazacort treatment of Duchenne muscular dystrophy, *J. Pediatr.*, 138:45-50 (2001).
Carter, Adeno-associated virus vectors, *Curr. Opin. Biotechnol.*, 3(5):533-9 (1992).
Cirak et al., Exon skipping and dystrophin restoration in patients with Duchenne muscular dystrophy after systemic phosphorodiamidate morpholino oligomer treatment: an open-label, phase 2, dose-escalation study, *Lancet*, 378:595-605 (2011).

(Continued)

*Primary Examiner* — Quang Nguyen
(74) *Attorney, Agent, or Firm* — Marshall, Gerstein & Borun LLP

(57) ABSTRACT

The present invention relates to recombinant adeno-associated virus (rAAV) delivery of polynucleotides for treating Duchenne Muscular Dystrophy resulting from the duplication of DMD exon 2. The invention provides rAAV products and methods of using the rAAV in the treatment of Duchenne Muscular Dystrophy.

14 Claims, 25 Drawing Sheets

(56) References Cited

OTHER PUBLICATIONS

Clark et al., A stable cell line carrying adenovirus-inducible rep and cap genes allows for infectivity titration of adeno-associated virus vectors, *Gene Therapy*, 3:1124-32 (1996).

Clark et al., Highly purified recombinant adeno-associated virus vectors are biologically active and free of detectable helper and wild-type viruses, *Hum. Gene Ther.*, 10(6)1031-9 (1999).

Cserjesi et al., Myogenin induces the myocyte-specific enhancer binding factor MEF-2 independently of other muscle-specific gene products, *Mol. Cell. Biol.*, 11:4854-62 (1991).

Dent et al., Improved molecular diagnosis of dystrophinopathies in an unselected clinical cohort, *Am. J. Med. Genet.*, 134(3): 295-8 (2005).

Exon Skipping Strategies for the Treatment of Duplication Mutations in Duchenne Muscular Dystrophy,<http://support.cureduchenne.org/site/P>CureDuchenne (2012).

Flanigan et al., Mutational spectrum of DMD mutations in dystrophinopathy patients: application of modern diagnostic techniques to a large cohort, *Hum. Mutat.*, 30(12):1657-66 (2009).

Gao et al., Clades of Adeno-associated viruses are widely disseminated in human tissues, *J. Virol.*, 78: 6381-8 (2004).

GenBank Accession Nos. AX753249, Sequence 4 from Patent EP1310571, dated Jun. 23, 2003.

Goemans et al., Systemic administration of PRO051 in Duchenne's muscular dystrophy, *New Engl. J. Med.*, 364:1513-22 (2011).

Goyenvalle et al., Engineering Exon-Skipping Vectors Expressing U7 snRNA Constructs for Duchenne Muscular Dystrophy Gene Therapy, *Mus. Gene Ther.*, 306(5702):179-96 (2011).

Goyenvalle et al., Rescue of dystrophicmuscle through U7 snRNA-mediated exon skipping, *Sci.*, 306(5702):1796-9 (2004).

Goyenvalle et al., Rescue of severely affected dystrophin/utrophin-deficient mice through scAAV-U7snRNA-mediated exon skipping, *Hum. Molec. Gen.*, 21(11):2559-71 (2012).

Goyenvalle et al., Therapeutic approaches to muscular dystrophy, *Hum. Molec. Gen.*, 20(R1):R69-78 (2011).

Greer et al., Targeted Exon Skipping to Correct Exon Duplications in the Dystrophin Gene, *Molec. Ther. Nuc. Acids*, 3:e155 (2014).

Hakim et al., The passive mechanical properties of the extensor digitorum longus muscle are compromised in 2- to 20-mo-old mdx mice, *J. Appl. Physiol.*, 110:1656-63 (1985).

Hermonat et al., Use of adeno-associated virus as a mammalian DNA cloning vector: transduction of neomycin resistance into mammalian tissue culture cells, *Proc. Natl. Acad. Sci. USA*, 81:6466-70 (1984).

Janssen et al., Utrophin deficiency worsens cardiac contractile dysfunction present in dystrophin-deficient mdx mice, *Am. J. Physiol. Heart Circ. Physiol.*, 289(6):H2373-8 (2005).

Johnson et al., Muscle creatine kinase sequence elements regulating skeletal and cardiac muscle expression in transgenic mice, *Mol. Cell. Biol.*, 9:3393-9 (1989).

Laughlin et al., Cloning of infectious adeno-associated virus genomes in bacterial plasmids, *Gene*, 23:65-73 (1983).

Lebkowski et al., Adeno-associated virus: a vector system for efficient introduction and integration of DNA into a variety of mammalian cell types, *Mol. Cell. Biol.*, 7:3988-96-(1988).

De et al., High Levels of Persistent Expression of α1-Antitrypsin Mediated by the Nonhuman Primate Serotype rh. 10 Adeno-associated Virus despite preexisting immunity to Common Human Adeno-associated Viruses,*Molec. Ther.*, 13(1):67-76 (2006).

Mader et al., A steroid-inducible promoter for the controlled overexpression of cloned genes in eukaryotic cells, *Proc. Natl. Acad. Sci. USA*, 90:5603-7 (1993).

Martin et al., Multi-confocal fluorescence correlation spectroscopy, *Am. J. Physiol. Cell. Physiol.*, 296:476-88 (2009).

McLaughlin et al., Adeno-associated virus general transduction vectors: analysis of proviral structures, *J. Virol.*, 62:1963 (1988).

Mendell et al., Randomized, double-blind six-month trial of prednisone in Duchenne's muscular dystrophy, *N. Engl. J. Med.*, 320:1592-7 (1989).

Mori et al., Two novel adeno-associated viruses from cynomolgus monkey: pseudotyping characterization of capsid protein, *Virology*, 330(2): 375-83 (2004).

Muscat et al., Multiple 5'-flanking regions of the human alpha-skeletal actin gene synergistically modulate muscle-specific expression, *Mol. Cell. Biol.*, 7:4089-99 (1987).

Muzyczka, Use of Adeno-Associated Virus as a General Transduction Vector for Mammalian Cells, *Curr. Top. Microbiol. Immunol.*, 158:97-129 (1992).

Paul et al., Increased viral titer through concentration of viral harvests from retroviral packaging lines, *Hum. Gene Ther.*, 4:609-15 (1993).

Perrin et al., An experimental rabies vaccine produced with a new BHK-21 suspension cell culture process: use of serum-free medium and perfusion-reactor system, *Vaccine*, 13:1244-50 (1995).

Rabinowitz et al., Cross-packaging of a single adeno-associated virus (AAV) type 2 vector genome into multiple AAV serotypes enables transduction with broad specificity, *J. Virol.*, 76:791-801 (2002).

Rodino-Klapac et al., Persistent expression of FLAG-tagged micro dystrophin in nonhuman primates following intramuscular and vascular delivery, *Mol. Ther.*, 18(1):109-17 (2010).

Samulski et al., Cloning of adeno-associated virus into pBR322: rescue of intact virus from the recombinant plasmid in human cells, *Proc. Natl. Acad. Sci. USA.*, 79:2077-81 (1982).

Samulski et al., Helper-free stocks of recombinant adeno-associated viruses: normal integration does not require viral gene expression, *J. Virol.*, 63:3822-8 (1989).

Schenpp et al., Highly purified recombinant adeno-associated virus vectors. Preparation and quantitation, *Methods Mol. Med.*, 69:427-43 (2002).

Semenza et al., Hypoxia-inducible nuclear factors bind to an enhancer element located 3' to the human erythropoietin gene, *Proc. Natl. Acad. Sci. USA*, 88: 5680-4 (1991).

Senapathy et al., Molecular cloning of adeno-associated virus variant genomes and generation of infectious virus by recombination in mammalian cells, *J. Biol. Chem.*, 259:4661-6 (1984).

Spurney et al, Preclinical drug trials in the mdx mouse: assessment of reliable and sensitive outcome measures, *Muscle & Nerve*, 39:591-602 (2009).

Srivastava et al., Nucleotide Sequence and Organization of the Adeno-Associated Virus 2 Genome, *J. Virol.*, 45:555-64 (1983).

Tratschin et al., A Human parvovirus, Adeno-Associated Virus, as a Eucaryotic Vector: Transient Expression and Encapsidation of the Procaryotic Gene for Chloramphenicol Acetyltransferase, *Mol. Cell. Biol.* 4:2072 (1984).

Tratschin et al., Adeno-associated virus vector for high-frequency integration, expression, and rescue of genes in mammalian cells, *Mol. Cell. Biol.*, 5:3251 (1985).

Vulin et al., A New Mouse Model of DMD: A Tool for Therapeutic Development Directed at Exon Duplications, *Molec. Ther.*, 21(Suppl. 1) (2013).

Wang et al., Recombinant AAV serotype 1 transduction efficiency and tropism in the murine brain, *Gene. Ther.*, 10:1528-34 (2003).

Weintraub et al., The myoD gene family: nodal point during specification of the muscle cell lineage, *Science*, 251:761-6 (1991).

White et al., Duplications in the DMD gene, *Hum. Mut.*, 27(9):938-45 (2006).

Xu et al., Postnatal overexpression of the CT GaINAc transferase inhibits muscular dystrophy in mdx mice without altering muscle growth or neuromuscular development: evidence for a utrophin-independent mechanism, *Neuromusc. Dis.*, 17:209-20 (2007).

* cited by examiner

FIGURE 7A

```
5'  ACGGGGGTCAAATCCATGGTGCTGGGCCGCTTCCTGAGTCAGATTCGGGA
    +++++|+++++|+++++|+++++|+++++|+++++|+++++|+++++|+   550
                          Rep

5'  CAAGCTGGTGCAGACCATCTACCGCGGGATCGAGCCGACCCTGCCCAACT
    +++++|+++++|+++++|+++++|+++++|+++++|+++++|+++++|+   600
                          Rep

5'  GGTTCGCGGTGACAAAGACGCGTAATGGCGCCGGAGGGGGGAACAAGGTG
    +++++|+++++|+++++|+++++|+++++|+++++|+++++|+++++|+   650
                          Rep

5'  GTGGACGAGTGCTACATCCCCAACTACCTGCTGCCCAAGACTCAGCCGGA
    +++++|+++++|+++++|+++++|+++++|+++++|+++++|+++++|+   700
                          Rep

5'  GCTGCAGTGGGCGTGGACTAACATGGAGGAGTATATAAGCGCGTGCTTGA
    +++++|+++++|+++++|+++++|+++++|+++++|+++++|+++++|+   750
                          Rep
                                            TATA Box

5'  ACCTGGCCGAGCCGCAAACGGCTCGTGGCCGCAGCACCTGACCCACGTCAGC
    +++++|+++++|+++++|+++++|+++++|+++++|+++++|+++++|+   800
                          Rep
        IP1

5'  CAGACCCAGGAGCAGAACAAGGAGAATCTGAACCCGAATTCTGACGCGCC
    +++++|+++++|+++++|+++++|+++++|+++++|+++++|+++++|+   850
                          Rep

5'  TGTCATCCGGTCAAAAACCTCCGCGCGCTACATGGAGCTGGTCGGGTGGC
    +++++|+++++|+++++|+++++|+++++|+++++|+++++|+++++|+   900
                          Rep
                                        Rep 52 ORF
```

FIGURE 7B

```
5' TGGTGGACCGGGGCATCACCTCCGAGAAGCAGTGGATCCAGGAGGACCAG
   +---+---+---+---+---+---+---+---+---+---+---+---+---+  950
                          Rep
                        Rep 52 ORF

5' GCCTCGTACATCTCCTTCAACGCCGCCTCCAACTCGCGGTCTCAGATCAA
   +---+---+---+---+---+---+---+---+---+---+---+---+---+  1000
                          Rep
                        Rep 52 ORF

5' GGCCGCGCTGGACAATGCCGGCAAGATCATGGCGCTGACCAAATCCGCGC
   +---+---+---+---+---+---+---+---+---+---+---+---+---+  1050
                          Rep
                        Rep 52 ORF

5' CCGACTACCTGGTAGGCCCCCCTCTCCCCCCCGACATTAAATCCAACCCC
   +---+---+---+---+---+---+---+---+---+---+---+---+---+  1100
                          Rep
                        Rep 52 ORF

5' ATCTACCGCATCCTGGAGCTGAATGGCTACGACCCTGCCTACGCCGGTTC
   +---+---+---+---+---+---+---+---+---+---+---+---+---+  1150
                          Rep
                        Rep 52 ORF

5' CGTCTTTCTCGGCTGGGCCCAGAAAAAGTTTGGCAAAAGGAACACCATCT
   +---+---+---+---+---+---+---+---+---+---+---+---+---+  1200
                          Rep
                        Rep 52 ORF

5' GGCTGTTTGGGCCGGCCACCACGGGCAAGACCAACATCGCGGAAGCCATC
   +---+---+---+---+---+---+---+---+---+---+---+---+---+  1250
                          Rep
                        Rep 52 ORF
```

FIGURE 7C

```
5' GCCCACGCCGTGCCCTTCTACGGCTGCGTCAACTGGACCAATGAGAACTT
                                                        1300
                        Rep
                      Rep 52 ORF

5' TCCCTTCAACCAGTCCGTCCACAAGATGCTCGTCTGGTCCAGGACCCCA
                                                        1350
                        Rep
                      Rep 52 ORF

5' AGATGACGGCCAAGGTCGTGGAGTCCGCCAAGGCCATTCTCGGCGGCAGC
                                                        1400
                        Rep
                      Rep 52 ORF

5' AAGCTCCGCCCTGGACCAAAACTCCAACTCCTCCCCCCAGATCCATCCAC
                                                        1450
                        Rep
                      Rep 52 ORF

5' CCCCGTGATCGTCACCTCCAACACCAACATGTGCGCCGTGATTGACGGGA
                                                        1500
                        Rep
                      Rep 52 ORF

5' ACAGCACCACCTTCGAGCACCAGCAGCCCTTGCAGGACCGCATGTTCAAA
                                                        1550
                        Rep
                      Rep 52 ORF

5' TTTGAACTTACCCGCCGTCTGGAGCACGACTTTGGCAAGGTGACAAAGCA
                                                        1600
                        Rep
                      Rep 52 ORF
```

```
5' CCACGCACCCCGCCCTGGAGCACGACAAGGGCTACCACCAGCACTCCAAG
                                                              2350
                        Cap

5' CGGGTGACAATGCGTACCTGCGGTATAATCACGGCCGACGCCCGAGTTTCAG
                                                              2400
                        Cap

5' GAGCGTCTGCAAGAAGATACGTCTTTTGGGGGCAACCTCGGGCGCGCAGT
                                                              2450
                        Cap

5' CTTCCAGGCCAAAAAGCGGGTTCTCGAACCTCTGGGGCCTGGTTGAATCGC
                                                              2500
                        Cap

5' CGGTTAAGACGGCTCCTGGAAAGAAGAGACCGGTAGAGCCATCACCCCAG
                                                              2550
                        Cap
   [■]

5' CCCTCTCCAGACTCCTCTACGGGCATCGGCAAGAAAGGCCAGCAGCCCGC
                                                              2600
                        Cap

5' AAAAAGAGACTCAATTTTGGGCAGACTGGCGACTCAGAGTCAGTCCCCG
                                                              2650
                        Cap

5' ACCCTCAACCAATGGAGAACCACCAGCAGCCCCTCTGGTCTGGATCT
                                                              2700
                        Cap

5' GGTACAATGGCTGCAGGCGGTGGCGCTCCAATGGCAGACAATAACGAAGG
                                                              2750
                        Cap
   [■]
```

FIGURE 7G

```
5' CGCCGACGGAGTGGGTAGTTCCTCAGGAAATTGGCATTGCGATTCCACAT
   ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼ 2800
                          Cap

5' GGCTGGGCGACAGAGTCATCACCACCAGCACCCGCACCTGGGCCCTGCCC
   ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼ 2850
                          Cap

5' ACCTACAACAACCACCTCTACAAGCAAATCTCCAACGGGACCTCGGGAGG
   ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼ 2900
                          Cap

5' AAGCACCAACGACAACACCTACTTCGGCTACAGCACCCCCTGGGGGTATT
   ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼ 2950
                          Cap

5' TTGACTTCAACAGATTCCACTGCCACTTTTCACCACGTGACTGGCAGCGA
   ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼ 3000
                          Cap

5' CTCATCAACAACAACTGGGGATTCCGGCCCAAGAGGCTCAACTTCAAGCT
   ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼ 3050
                          Cap

5' CTTCAACATCCAAGTCAAGGAGGTCACGCAGAATGAAGGCACCAAGACCA
   ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼ 3100
                          Cap

5' TCGCCAATAACCTTACCAGCACGATTCAGGTCTTTACGGACTCGGAATAC
   ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼ 3150
                          Cap

5' CAGCTCCCGTACGTGCTCGGCTCGGCGCACCAGGGCTGCCTGCCTCCGTT
   ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼ 3200
                          Cap
```

FIGURE 7H

```
5'  CCCGGCGGACGTCTTCATGATTCCTCAGTACGGGTACCTGACTCTGAACA
    ++++++++++++++++++++++++++++++++++++++++++++++++++  3250
                            Cap

5'  ATGGCAGTCAGGCTGTGGGCCGGTCGTCCTTCTACTGCCTGGAGTACTTT
    ++++++++++++++++++++++++++++++++++++++++++++++++++  3300
                            Cap

5'  CCTTCTCAAATGCTGAGAACGGGCAACAACTTTGAATTCAGCTACAACTT
    ++++++++++++++++++++++++++++++++++++++++++++++++++  3350
                            Cap

5'  CGAGGACGTGCCCTTCCACAGCAGCTACGCGCACAGCCAGAGCCTGGACC
    ++++++++++++++++++++++++++++++++++++++++++++++++++  3400
                            Cap

5'  GGCTGATGAACCCTCTCATCGACCAGTACTTGTACTACCTGTCCCGGACT
    ++++++++++++++++++++++++++++++++++++++++++++++++++  3450
                            Cap

5'  CAAAGCACGGGCGGTACTGCAGGAACTCAGCAGTTGCTATTTCTCAGGC
    ++++++++++++++++++++++++++++++++++++++++++++++++++  3500
                            Cap

5'  CGGGCCTAACAACATGTCGGCTCAGGCCAAGAACTGGCTACCCGGTCCCT
    ++++++++++++++++++++++++++++++++++++++++++++++++++  3550
                            Cap

5'  GCTACCGGCAGCAACGCGTCTCCACGACACTGTCGCAGAACAACAACAGC
    ++++++++++++++++++++++++++++++++++++++++++++++++++  3600
                            Cap

5'  AACTTTGCCTGGACGGGTGCCACCAAGTATCATCTGAATGGCAGAGACTC
    ++++++++++++++++++++++++++++++++++++++++++++++++++  3650
                            Cap
```

FIGURE 7I

```
5'  TCTGGTGAATCCTGGCGTTGCCATGGCTACCCACAAGGACGACGAAGAGC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  3700
                        Cap

5'  GATTTTTCCATCCAGCGGAGTCTTAATGTTTGGGAAACAGGGAGCTGGA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  3750
                        Cap

5'  AAAGACAACGTGGACTATAGCAGCGTGATGCTAACCAGCGAGGAAGAAAT
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  3800
                        Cap

5'  AAAGACCACCAACCCAGTGGCCACAGAACAGTACGGCGTGGTGGCCGATA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  3850
                        Cap

5'  ACCTGCAACAGCAAAACGCCGCTCCTATTGTAGGGGCCGTCAATAGTCAA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  3900
                        Cap

5'  GGAGCCTTACCTGGCATGGTGTGGCAGAACCGGCACGTGTACCTGCAGGG
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  3950
                        Cap

5'  TCCCATCTGGGCCAAGATTCCTCATACGGACGGCAACTTTCATCCCTCGC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  4000
                        Cap

5'  CGCTGATGGGAGGCTTTGGACTGAAGCATCCGCCTCCTCAGATCCTGATT
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  4050
                        Cap

5'  AAAACACACCTGTTCCCGCGGATCCTCCGACCACCTTCAATCAGGCCAA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  4100
                        Cap
```

FIGURE 7J

```
5'   GCTGGCTTCTTTCATCACGCAGTACAGTACCGGCCAGGTCAGCCGTGGAGA
     ++++|++++|++++|++++|++++|++++|++++|++++|++++|++++|   4150
     ─────────────────────Cap─────────────────────────

5'   TCGAGTGGGAGCTGCAGAAGGAGAACAGCAAACGCTGGAACCCAGAGATT
     ++++|++++|++++|++++|++++|++++|++++|++++|++++|++++|   4200
     ─────────────────────Cap─────────────────────────

5'   CAGTACACTTCCAACTACTACAAATCTACAAATGTGGACTTTGCTGTCAA
     ++++|++++|++++|++++|++++|++++|++++|++++|++++|++++|   4250
     ─────────────────────Cap─────────────────────────

5'   TACTGAGGGTACTTATTCCGAGCCTCGCCCCATTGGCACCCGTTACCTCA
     ++++|++++|++++|++++|++++|++++|++++|++++|++++|++++|   4300
     ─────────────────────Cap─────────────────────────

5'   CCCGTAATCTGTAATTACATGTTAATCAATAAACCGGTTAATTCGTTTCA
     ++++|++++|++++|++++|++++|++++|++++|++++|++++|++++|   4350
     ──── Cap ────

5'   GTTCAACTTTGGTCTCCTGTCCTTCTTATCTTATCGGTTACCATAGAAAC
     ++++|++++|++++|++++|++++|++++|++++|++++|++++|++++|   4400

5'   TGGTTACTTATTAACTGCTTGGTGCGCTTCGCGATAAAGACTTACGTCA
     ++++|++++|++++|++++|++++|++++|++++|++++|++++|++++|   4450

5'   TCGGGTTACCCCTAGTGATGGA
     ++++|++++|++++|++++|++   4472
     ←────── D ──────→
```

FIGURE 7K

Legend:

ATCG: inverted terminal sequence (ITR)

ATCG:U7-Along (antisense sequence in capital letters) (first copy)

U7-C (antisense sequence in capital letters)(first copy)

U7-C (antisense sequence in capital letters)(second copy)

ATCG:U7-Along (antisense sequence in capital letters) (second copy)

ATCG: inverted terminal sequence 3'(ITR)

ctgcgcgctcgctcgctcactgaggccgcccgggcaaagcccgggcgtcgggcgacctttgtcgcccgacctcagtgagcgagcgag
cgcgcagagagggagtgggggttgtacacatacgtttcctatgaatgacagacagaggatcaaagcccctctcacacaccgcggagcgt
ggangagactgttttgcttcattgtagaccagtgaaattggaggggttttccgaccgaagtcagaaaactgCTCCAAAATTt
acATGAAAGAGAAGATCTTCAAAAGAAAACttgcggaagtgctgtgtagcagccagggAaggacatcaa
ctccacttcgatgaggtgagatcaaggtgccattccacaccctccactgatatgtgaatcacaaagcacagttcctattcggtcgataa
acaatattctaaaagactattaaaaccgctcgtttcttgagtttgtgaccgcttgtaaaggctatgcaaatgagTcagtgctgattggctgaaa
cagccaatcacagctcctatgttgtta[...]ccacaccctccactgatatgtgaatcacaaagcacagttcctattcggtcgataa
acaatattctaaaagactattaaaaccgctcgtttcttgagtttgtgaccgcttgtaaaggctatgcaaatgagTcagtgctgattggctgaaa
cagccaatcacagctcctatgttgtta[...]ccacaccctccactgatatgtgaatcacaaagcacagttcctattcggtcgataa
acaatattctaaaagactattaaaaccgctcgtttcttgagtttgtgaccgcttgtaaaggctatgcaaatgagTcagtgctgattggctgaaa
cagccaatcacagctcctatgttgttaTCTAGCcacatacgcgtttctaggaaccagagaggatcaaagcccctctcacacaccg
gggagcggagcaagaactgttttgcttcattgtagaccagtgaaattggagggttttccgaccgaagtcagaaaactgCTCCA
AAATTacATGAAAGAGAAGATCTTCAAAAGAAAACttgcggaagtgctgtgtagcagccagggA
aggacatcaactccacttcgatgaggtgagatcaaggtgccattccacaccctccactgatatgtgaatcacaaagcacagttcctatt
cggtcgataaacaatattctaaaagactattaaaaccgctcgtttcttgagtttgtgaccgcttgtaaaggctatgcaaatgagTcagtgctga
ttggctgaaaacagccaatcacagctcctatgttgttatctagagcatggctacgtagataagtagcatggcgggttaatcattaactacagg
aacccctagtgatgagttggccactccctctgcgcgctcgctcgctcactgaggccgggcgaccaaaggtcgcccgacgcccgggct
ttgcccgggcggcctcagtgagcgagcgagcgcgccagc

FIGURE 9 c
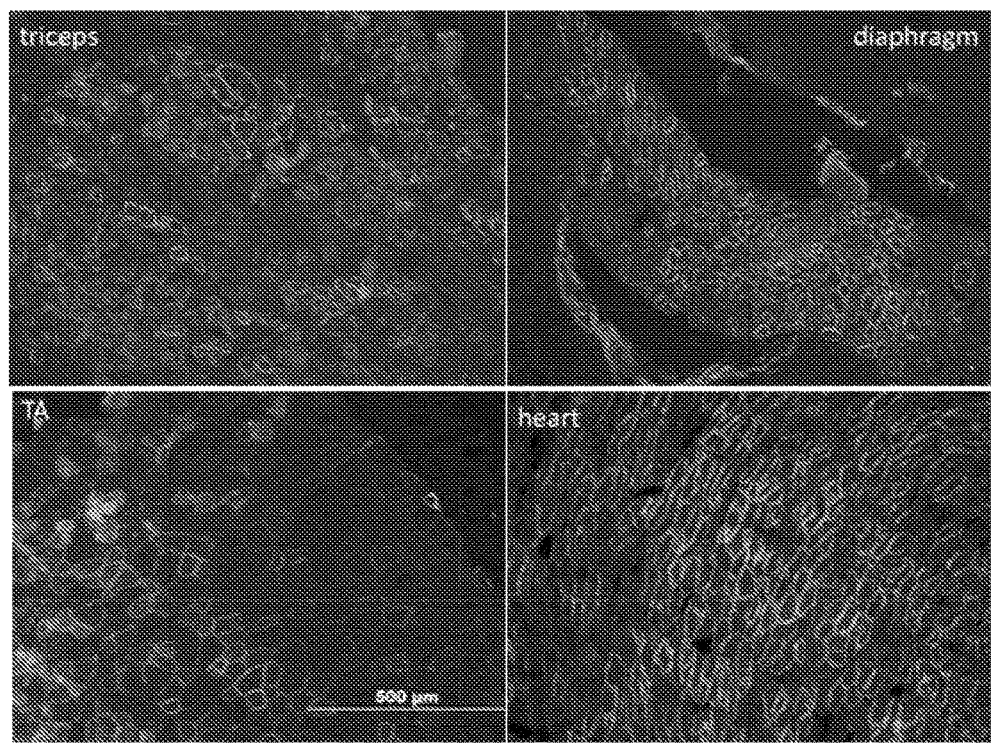
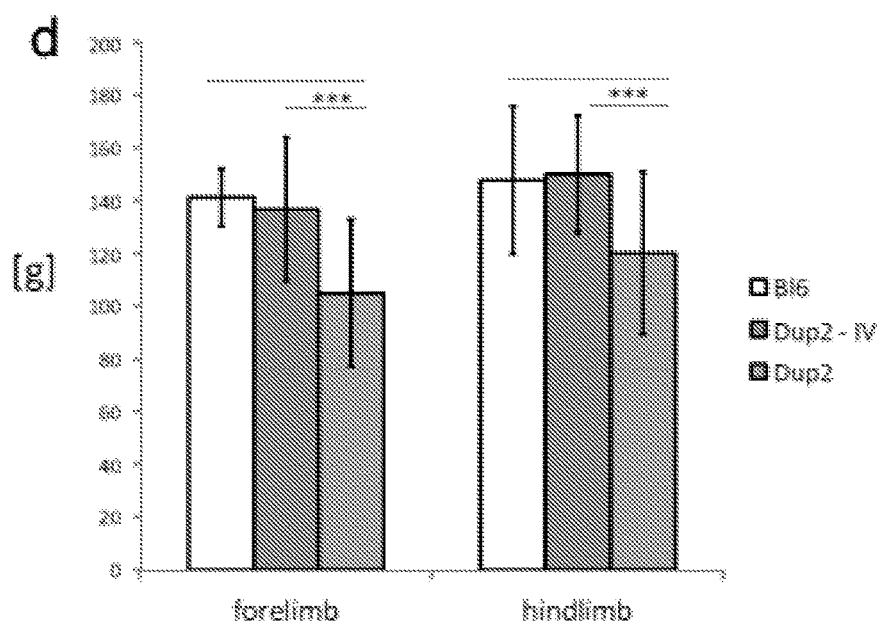
FIGURE 13

SEQUENCE LISTING

```
<160> NUMBER OF SEQ ID NOS: 6

<210> SEQ ID NO 1
<211> LENGTH: 4472
<212> TYPE: DNA
<213> ORGANISM: Adeno-associated virus

<400> SEQUENCE: 1
ctccatcact aggggtaacc gcgaagcgcc tcccacgctg ccgcgtcagc gctgacgtaa      60
attacgtcat aggggagtgg tcctgtatta gctgtcacgt gagtgctttt gcgacatttt     120
gcgacaccac gtggccattc atggtatata tggccgagtg agcgagcagg atctccattt     180
tgaccgcgaa atttgaacga gcagcagcca tgccgggctt ctacgagatc gtgcttaagg     240
tgccgagcga cctggacgag cacctgccgg gcatttctga ctcgtttgtg aactgggtgg     300
cagagaagga atgggagctg cccccggatt ctgacatgga tcggaatctg attgagcagg     360
cacccctgac cgtggccgag aagctacagc gcgacttcct ggtccaatgg cgccgcgtga     420
gtaaggcccc ggaggccctc ttctttgttc agttcgagaa gggcgagtcc tacttccacc     480
tccatattct ggtagagacc acgggggtca aatccatggt gctgggccgc ttcctgagtc     540
agattcggga caagctggtg cagaccatct accgcgggat cgagccgacc ctgcccaact     600
ggttcgcggt gacaaagacg cgtaatggcg ccggagggg gaacaaggtg gtggacgagt     660
gctacatccc caactacctg ctgcccaaga ctcagcccga gctgcagtgg gcgtggacta     720
acatggagga gtatataagc gcgtgcttga acctggccga gcgcaaacgg ctcgtggcgc     780
agcacctgac ccacgtcagc cagacccagg agcagaacaa ggagaatctg aacccgaatt     840
ctgacgcgcc tgtcatccgg tcaaaaacct ccgcgcgcta catggagctg gtcgggtggc     900
tggtggaccg gggcatcacc tccgagaagc agtggatcca ggaggaccag gcctcgtaca     960
```

```
tctccttcaa cgccgcctcc aactcgcggt ctcagatcaa ggccgcgctg acaatgccg   1020 gcaagatcat ggcgctgacc aaatccgcgc ccgactacct ggtaggcccc gctctgcccg   1080
cggacattaa atccaaccgc atctaccgca tcctggagct gaatggctac gaccctgcct   1140
acgccggttc cgtctttctc ggctgggccc agaaaaagtt tggcaaaagg aacaccatct   1200
ggctgtttgg gccggccacc acgggcaaga ccaacatcgc ggaagccatc gcccacgccg   1260
tgcccttcta cggctgcgtc aactggacca atgagaactt tcccttcaac gattgcgtcg   1320
acaagatggt gatctggtgg gaggagggca agatgacggc caaggtcgtg gagtccgcca   1380
aggccattct cggcggcagc aaggtgcgcg tggaccaaaa gtgcaagtcg tccgcccaga   1440
tcgatcccac ccccgtgatc gtcacctcca acaccaacat gtgcgccgtg attgacggga   1500
acagcaccac cttcgagcac cagcagccgt tgcaggaccg gatgttcaaa tttgaactta   1560
cccgccgtct ggagcacgac tttggcaagg tgacaaagca ggaagtcaaa gagttcttcc   1620
gctgggcgca ggatcacgtg accgaggtgg cgcatgagtt ctacgtcaga aagggtggag   1680
ctaacaaaag acccgccccc gatgacgcgg atataagcga gcccaagcgg gcctgccccct   1740 cagtcgcgga tccatcgacg tcagacgcgg aaggagctcc ggtggacttt gccgacaggt   1800
accaaaacaa atgttctcgt cacgcgggca tgcttcagat gctgtttccc tgcaaaacat   1860
gcgagagaat gaatcagaat ttcaacattt gcttcacgca cgggaccaga gactgttcag   1920
aatgtttccc tggcgtgtca gaatctcaac cggtcgtcag aaaaaagacg tatcggaaac   1980
tctgtgcgat tcatcatctg ctggggcggg cacccgagat tgcttgctcg gcctgcgacc   2040
tggtcaacgt ggacctggat gactgtgttt ctgagcaata aatgactaa accaggtatg   2100 gctgccgatg gttatcttcc agattggctc gaggacaacc tctctgaggg cattcgcgag   2160
tggtgggacc tgaaacctgg agcccgaaa cccaaagcca accagcaaaa gcaggacaac   2220
ggccggggtc tggtgcttcc tggctacaag tacctcggac ccttcaacgg actcgacaag   2280
ggggagcccg tcaacgcggc ggacgcagcg ccctcgagc acgacaaggc ctacgaccag   2340
cagctccaag cgggtgacaa tccgtacctg cggtataatc acgccgacgc cgagtttcag   2400
gagcgtctgc aagaagatac gtcttttggg ggcaacctcg ggcgcgcagt cttccaggcc   2460
aaaaagcggg ttctcgaacc tctgggcctg gttgaatcgc cggttaagac ggctcctgga   2520
aagaagagac cggtagagcc atcacccag cgctctccag actcctctac gggcatcggc   2580
aagaaaggcc agcagcccgc aaaaaagaga ctcaattttg ggcagactgg cgactcagag   2640
tcagtccccg accctcaacc aatcggagaa ccaccagcag gccctctgg tctgggatct   2700 ggtacaatgg ctgcaggcgg tggcgctcca atggcagaca taacgaagg cgccgacgga   2760 gtgggtagtt cctcaggaaa ttggcattgc gattccacat ggctgggcga cagagtcatc   2820
accaccagca cccgcacctg ggccctgccc acctacaaca accacctcta caagcaaatc   2880
tccaacggga cctcgggagg aagcaccaac gacaacacct acttcggcta cagcaccccc   2940
tgggggtatt ttgacttcaa cagattccac tgccactttt caccacgtga ctggcagcga   3000
ctcatcaaca caactggggg attccggccc aagaggctca acttcaagct cttcaacatc   3060
caagtcaagg aggtcacgca gaatgaaggc accaagacca tcgccaataa ccttaccagc   3120
acgattcagg tctttacgga ctcggaatac cagctcccgt acgtgctcgg ctcggcgcac   3180
cagggctgcc tgcctccgtt cccggcggac gtcttcatga ttcctcagta cgggtacctg   3240
actctgaaca atggcagtca ggctgtgggc cggtcgtcct tctactgcct ggagtacttt   3300
ccttctcaaa tgctgagaac gggcaacaac tttgaattca gctacaactt cgaggacgtg   3360
```

```
cccttccaca gcagctacgc gcacagccag agcctggacc ggctgatgaa ccctctcatc    3420
gaccagtact tgtactacct gtcccggact caaagcacgg gcggtactgc aggaactcag    3480
cagttgctat tttctcaggc cgggcctaac aacatgtcgg ctcaggccaa gaactggcta    3540
cccggtccct gctaccggca gcaacgcgtc tccacgacac tgtcgcagaa caacaacagc    3600
aactttgcct ggacgggtgc caccaagtat catctgaatg cagagactc tctggtgaat    3660 cctggcgttg ccatggctac ccacaaggac gacgaagagc gatttttcc atccagcgga    3720 gtcttaatgt ttgggaaaca gggagctgga aaagacaacg tggactatag cagcgtgatg    3780
ctaaccagcg aggaagaaat aaagaccacc aacccagtgg ccacagaaca gtacggcgtg    3840
gtggccgata acctgcaaca gcaaaacgcc gctcctattg taggggccgt caatagtcaa    3900
ggagccttac ctggcatggt gtggcagaac cgggacgtgt acctgcaggg tcccatctgg    3960
gccaagattc ctcatacgga cggcaacttt catccctcgc cgctgatggg aggctttgga    4020
ctgaagcatc cgcctcctca gatcctgatt aaaaacacac tgttcccgc ggatcctccg    4080 accaccttca ctaaggccaa gctggcttct ttcatcacgc agtacagtac cggccaggtc    4140
agcgtggaga tcgagtggga gctgcagaag gagaacagca aacgctggaa cccagagatt    4200
cagtacactt ccaactacta caaatctaca aatgtggact ttgctgtcaa tactgagggt    4260
acttattccg agcctcgccc cattggcacc cgttacctca cccgtaatct gtaattacat    4320
gttaatcaat aaaccggtta attcgtttca gttgaacttt ggtctcctgt ccttcttatc    4380
ttatcggtta ccatagaaac tggttactta ttaactgctt ggtgcgcttc gcgataaaag    4440
acttacgtca tcgggttacc cctagtgatg ga                                  4472

<210> SEQ ID NO 2
<211> LENGTH: 2052
<212> TYPE: DNA
<213> ORGANISM: Adeno-associated virus
<220> FEATURE:
<221> NAME/KEY: misc_feature
<222> LOCATION: (1)..(88)
<223> OTHER INFORMATION: Inverted Terminal Sequence (ITR)
<220> FEATURE:
<221> NAME/KEY: misc_feature
<222> LOCATION: (89)..(365)
<223> OTHER INFORMATION: U7-Along
<220> FEATURE:
<221> NAME/KEY: misc_feature
<222> LOCATION: (525)..(806)
<223> OTHER INFORMATION: U7-C
<220> FEATURE:
<221> NAME/KEY: misc_feature
<222> LOCATION: (961)..(1242)
<223> OTHER INFORMATION: U7-C
<220> FEATURE:
<221> NAME/KEY: misc_feature
<222> LOCATION: (1397)..(1678)
<223> OTHER INFORMATION: U7-Along
<220> FEATURE:
<221> NAME/KEY: misc_feature
<222> LOCATION: (1830)..(2052)
<223> OTHER INFORMATION: Inverted Terminal Sequence 3' (ITR)

<400> SEQUENCE: 2
ctgcgcgctc gctcgctcac tgaggccgcc cgggcaaagc ccgggcgtcg ggcgaccttt     60
ggtcgcccgg cctcagtgag cgagcgagcg cgcagagagg gagtggggtt gtacacatac    120
gcgtttccta ggaaaccaga gaaggatcaa agcccctctc acacccgggg agcggggaa     180 gagaactgtt ttgctttcat tgtagaccag tgaaattggg aggggttttc cgaccgaagt    240
```

```
cagaaaacct gctccaaaaa tttagatgaa agagaagatc ttcaaaagaa aacttgcgga      300
agtgcgtctg tagcgagcca gggaaggaca tcaactccac tttcgatgag ggtgagatca      360
aggtgccatt tccacacccc tccactgata tgtgaatcac aaagcacagt tccttattcg      420
gttcgataaa caatattcta aaagactatt aaaccgctc gtttcttgag tttgtgaccg       480
cttgtaaagg ctatgcaaat gagtcagtgc tgattggctg aaaacagcca atcacagctc      540
ctatgttgtt atctagccac atacgcgttt cctaggaaac cagagaagga tcaaagcccc      600
tctcacacac cggggagcgg ggaagagaac tgttttgctt tcattgtaga ccagtgaaat      660 tgggagggg tttccgaccg aagtcagaaa acctgctcca aaaattgcac aattttctaa       720
ggtaagaatt tgcggaagtg cgtctgtagc gagccaggga aggacatcaa ctccactttc      780
gatgagggtg agatcaaggt gccatttcca caccctcca ctgatatgtg aatcacaaag       840
cacagttcct tattcggttc gataaacaat attctaaaag actattaaaa ccgctcgttt      900
cttgagtttg tgaccgcttg taaaggctat gcaaatgagt cagtgctgat tggctgaaaa      960
cagccaatca cagctcctat gttgttatct agccacatac gcgtttccta ggaaaccaga     1020
gaaggatcaa agcccctctc acacccggg gagcggggaa gagaactgtt tgctttcat      1080 tgtagaccag tgaaattggg aggggttttc cgaccgaagt cagaaaacct gctccaaaaa     1140
ttgcacaatt ttctaaggta agaatttgcg gaagtgcgtc tgtagcgagc agggaagga     1200 catcaactcc actttcgatg agggtgagat caaggtgcca tttccacacc cctccactga     1260
tatgtgaatc acaaagcaca gttccttatt cggttcgata acaatattc taaaagacta     1320 ttaaaaccgc tcgtttcttg agtttgtgac cgcttgtaaa ggctatgcaa atgagtcagt     1380
gctgattggc tgaaaacagc caatcacagc tcctatgttg ttatctagcc acatacgcgt     1440 tcctaggaa accagagaag gatcaaagcc cctctcacac accggggagc ggggaagaga      1500
actgttttgc tttcattgta gaccagtgaa attgggaggg gttttccgac cgaagtcaga     1560
aaacctgctc caaaaattta gatgaaagag aagatcttca aaagaaaact gcggaagtg     1620 cgtctgtagc gagccaggga aggacatcaa ctccactttc gatgagggtg agatcaaggt     1680
gccatttcca caccctcca ctgatatgtg aatcacaaag cacagttcct tattcggttc     1740
gataaacaat attctaaaag actattaaaa ccgctcgttt cttgagtttg tgaccgcttg     1800
taaaggctat gcaaatgagt cagtgctgat tggctgaaaa cagccaatca cagctcctat     1860
gttgttatct agagcatggc tacgtagata agtagcatgg cgggttaatc attaactaca     1920
aggaacccct agtgatggag ttggccactc cctctctgcg cgctcgctcg ctcactgagg     1980
ccgggcgacc aaaggtcgcc cgacgcccgg gctttgcccg gcggcctca gtgagcgagc      2040 gagcgcgcca gc                                                         2052

<210> SEQ ID NO 3
<211> LENGTH: 28
<212> TYPE: DNA
<213> ORGANISM: Adeno-associated virus

<400> SEQUENCE: 3
tcaaaagaaa acattcacaa aatgggta                                          28

<210> SEQ ID NO 4
<211> LENGTH: 31
<212> TYPE: DNA
<213> ORGANISM: Adeno-associated virus

<400> SEQUENCE: 4
```

```
gttttcttttt gaagatcttc tctttcatct a                              31

<210> SEQ ID NO 5
<211> LENGTH: 19
<212> TYPE: DNA
<213> ORGANISM: Adeno-associated virus

<400> SEQUENCE: 5
agatcttctc tttcatcta                                             19

<210> SEQ ID NO 6
<211> LENGTH: 23
<212> TYPE: DNA
<213> ORGANISM: Adeno-associated virus

<400> SEQUENCE: 6
gcacaatttt ctaaggtaag aat                                        23
```

RECOMBINANT ADENO-ASSOCIATED VIRUS DELIVERY OF EXON 2-TARGETED U7SNRNA POLYNUCLEOTIDE CONSTRUCTS

This application claims the benefit of the filing date of U.S. Provisional Patent Application No. 61/814,256 filed Apr. 20, 2013, which is incorporated by reference herein in its entirety.

FIELD OF THE INVENTION

The present invention relates to recombinant adeno-associated virus (rAAV) delivery of polynucleotides for treating Duchenne Muscular Dystrophy resulting from the duplication of DMD exon 2. The invention provides rAAV products and methods of using the rAAV in the treatment of Duchenne Muscular Dystrophy.

INCORPORATION BY REFERENCE OF THE SEQUENCE LISTING

This application contains, as a separate part of disclosure, a Sequence Listing in computer-readable form (filename: 47699PCT_SeqListing.txt; 10,162 bytes—ASCII text file, created 18 Apr. 2014) which is incorporated by reference herein in its entirety.

BACKGROUND

Muscular dystrophies (MDs) are a group of genetic diseases. The group is characterized by progressive weakness and degeneration of the skeletal muscles that control movement. Some forms of MD develop in infancy or childhood, while others may not appear until middle age or later. The disorders differ in terms of the distribution and extent of muscle weakness (some forms of MD also affect cardiac muscle), the age of onset, the rate of progression, and the pattern of inheritance.

One form of MD is Duchenne Muscular Dystrophy (DMD). It is the most common severe childhood form of muscular dystrophy affecting 1 in 5000 newborn males. DMD is caused by mutations in the DMD gene leading to absence of dystrophin protein (427 KDa) in skeletal and cardiac muscles, as well as GI tract and retina. Dystrophin not only protects the sarcolemma from eccentric contractions, but also anchors a number of signaling proteins in close proximity to sarcolemma. Many clinical cases of DMD are linked to deletion mutations in the DMD gene. Despite many lines of research following the identification of the DMD gene, treatment options are limited. Corticosteroids are clearly beneficial but even with added years of ambulation the benefits are offset by long-term side effects. The original controlled, randomized, double-blind study reported more than 20 years ago showed benefits using prednisone [Mendell et al., *N. Engl. J. Med.*, 320: 1592-1597 (1989)]. Subsequent reports showed equal efficacy using deflazacort, a sodium-sparing steroid [Biggar et al., *J. Pediatr.*, 138: 45-50 (2001)]. Recent studies also demonstrate efficacy by exon skipping, prolonging walking distance on the 6MWT. Thus far, published clinical studies have reported benefit for only mutations where the reading frame is restored by skipping exon 51 [Cirak et al., *Lancet*, 378: 595-605 (2011) and Goemans et al., *New Engl. J. Med.* 364: 1513-1522 (2011)]. In the only report of a double blind, randomized treatment trial promising results were demonstrated with eteplirsen, a phosphorodiamidate morpholino oligomer (PMO). In all of these exon-skipping trials, the common denominator of findings has been a plateau in walking ability after an initial modest improvement.

See also, U.S. Patent Application Publication Nos. 2012/0077860 published Mar. 29, 2012; 2013/0072541 published Mar. 21, 2013; and 2013/0045538 published Feb. 21, 2013.

In contrast to the deletion mutations, DMD exon duplications account for around 5% of disease-causing mutations in unbiased samples of dystrophinopathy patients [Dent et al., *Am. J. Med. Genet.*, 134(3): 295-298 (2005)], although in some catalogues of mutations the number of duplications is higher [including that published by the United Dystrophinopathy Project in Flanigan et al., *Hum. Mutat.*, 30(12): 1657-1666 (2009), in which it was 11%].

Adeno-associated virus (AAV) is a replication-deficient parvovirus, the single-stranded DNA genome of which is about 4.7 kb in length including 145 nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., *J. Virol.*, 45: 555-564 {1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively (see also U.S. Pat. Nos. 7,282,199 and 7,790,449 relating to AAV-8); the AAV-9 genome is provided in Gao et al., *J. Virol.*, 78: 6381-6388 (2004); the AAV-10 genome is provided in *Mol. Ther.*, 13(1): 67-76 (2006); and the AAV-11 genome is provided in *Virology*, 330(2): 375-383 (2004). Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

An AAV8-like AAV termed rh.74 to deliver DNAs encoding various proteins. Xu et al., *Neuromuscular Disorders*, 17: 209-220 (2007) and Martin et al., *Am. J. Physiol. Cell. Physiol.*, 296: 476-488 (2009) relate to rh.74 expression of cytotoxic T cell GalNAc transferase for Duchenne muscular dystrophy. Rodino-Klapac et al., *Mol. Ther.*, 18(1): 109-117 (2010) describes AAV rh.74 expression of a micro-dystrophin FLAG protein tag fusion after delivery of the AAV rh.74 by vascular limb perfusion.

The muscular dystrophies are a group of diseases without identifiable treatment that gravely impact individuals, families, and communities. The costs are incalculable. Individuals suffer emotional strain and reduced quality of life associated with loss of self-esteem. Extreme physical challenges resulting from loss of limb function creates hardships in activities of daily living. Family dynamics suffer through financial loss and challenges to interpersonal relationships. Siblings of the affected feel estranged, and strife between spouses often leads to divorce, especially if responsibility for the muscular dystrophy can be laid at the feet of one of the parental partners. The burden of quest to find a cure often becomes a life-long, highly focused effort that detracts and challenges every aspect of life. Beyond the family, the community bears a financial burden through the need for added facilities to accommodate the handicaps of the muscular dystrophy population in special education, special transportation, and costs for recurrent hospitalizations to treat recurrent respiratory tract infections and cardiac complications. Financial responsibilities are shared by state and federal governmental agencies extending the responsibilities to the taxpaying community.

There thus remains a need in the art for treatments for muscular dystrophies including DMD.

DESCRIPTION

The present invention provides methods and products for preventing, delaying the progression of, and/or treating DMD involving a duplication of exon 2 of the DMD gene. The methods involve using AAV as a delivery vector for a polynucleotide construct encoding a U7 small nuclear RNA and an exon 2 targeting antisense sequence, an "exon 2-targeted U7snRNA polynucleotide construct." For example, the polynucleotide construct is inserted in the genome of a rAAV rh.74, the genome of a rAAV6 or the genome of a rAAV9. The polynucleotide sequence of the AAV rh.74 genome is shown in FIG. 7 and SEQ ID NO: 1.

Exemplary exon 2 targeting antisense sequences include, but are not limited to,

U7B
(SEQ ID NO: 3)
TCAAAAGAAAACATTCACAAAATGGGTA;

-continued
U7Along
(SEQ ID NO: 4)
GTTTTCTTTTGAAGATCTTCTCTTTCATcta;

U7Ashort
(SEQ ID NO: 5)
AGATCTTCTCTTTCATcta;
and

U7C
(SEQ ID NO: 6)
GCACAATTTTCTAAGGTAAGAAT.

In one aspect, a method of ameliorating DMD in a patient is provided. In some embodiments, the method comprises the step of administering a rAAV to the patient, wherein the genome of the rAAV comprises an exon 2-targeted U7snRNA polynucleotide construct.

In yet another aspect, the invention provides a method of inhibiting the progression of dystrophic pathology associated with DMD. In some embodiments, the method comprises the step of administering a rAAV to the patient, wherein the genome of the rAAV comprises an exon 2-targeted U7snRNA polynucleotide construct.

In still another aspect, a method of improving muscle function in a patient afflicted with DMD is provided. In some embodiments, the method comprises the step of of administering a rAAV to the patient, wherein the genome of the rAAV comprises an exon 2-targeted U7snRNA polynucleotide construct. In some instances, the improvement in muscle function is an improvement in muscle strength. The improvement in muscle strength is determined by techniques known in the art such as the maximal voluntary isometric contraction testing (MVICT). In some instances, the improvement in muscle function is an improvement in stability in standing and walking. The improvement in stability strength is determined by techniques known in the art such as the 6-minute walk test (6MWT) or timed stair climb.

In another aspect, the invention provides a method of delivering an exon 2-targeted U7snRNA polynucleotide construct to an animal (including, but not limited to, a human). In some embodiments, the method comprises the step of a rAAV to the patient, wherein the genome of the rAAV comprises an exon 2-targeted U7snRNA polynucleotide construct.

Cell transduction efficiencies of the methods of the invention described above and below may be at least about 60, 65, 70, 75, 80, 85, 90 or 95 percent.

In some embodiments of the foregoing methods of the invention, the virus genome is a self-complementary genome. In some embodiments of the methods, the genome of the rAAV lacks AAV rep and cap DNA. In some embodiments of the methods, the rAAV is a SC rAAV U7_ACCA comprising the exemplary genome set out in FIG. 9. In some embodiments the rAAV is a rAAV rh.74. In some embodiments, the rAAV is a rAAV6. In some embodiments, the rAAV is a rAAV9.

In yet another aspect, the invention provides a rAAV comprising the AAV rh.74 capsid and a genome comprising the exemplary exon 2-targeted U7 snRNA polynucleotide construct U7_ACCA. In some embodiments, the genome of the rAAV lacks AAV rep and cap DNA. In some embodiments, the rAAV comprises a self-complementary genome. In some embodiments of the methods, the rAAV is a SC rAAV U7_ACCA comprising the exemplary genome is set out in FIG. 9. In some embodiments the rAAV is a rAAV rh.74. In some embodiments, the rAAV is a rAAV6. In some embodiments, the rAAV is a rAAV9.

Recombinant AAV genomes of the invention comprise one or more AAV ITRs flanking at least one exon 2-targeted U7 snRNA polynucleotide construct. Genomes with exon 2-targeted U7 snRNA polynucleotide constructs comprising each of the exon 2 targeting antisense sequences referred to above are specifically contemplated, as well as genomes with exon 2-targeted U7 snRNA polynucleotide constructs comprising each possible combination of two or more of the exon 2 targeting antisense sequences referred to above. In some embodiments, including the exemplified embodiments, the U7 snRNA polynucleotide includes its own promoter. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10 and AAV-11. As noted in the Background section above, the nucleotide sequences of the genomes of various AAV serotypes are known in the art. In some embodiments of the invention, the promoter DNAs are muscle-specific control elements, including, but not limited to, those derived from the actin and myosin gene families, such as from the myoD gene family [See Weintraub et al., *Science,* 251: 761-766 (1991)], the myocyte-specific enhancer binding factor MEF-2 [Cserjesi and Olson, *Mol. Cell. Biol.,* 11: 4854-4862 (1991)], control elements derived from the human skeletal actin gene [Muscat et al., *Mol. Cell. Biol.,* 7: 4089-4099 (1987)], the cardiac actin gene, muscle creatine kinase sequence elements [Johnson et al., *Mol. Cell. Biol.,* 9:3393-3399 (1989)] and the murine creatine kinase enhancer (MCK) element, desmin promoter, control elements derived from the skeletal fast-twitch troponin C gene, the slow-twitch cardiac troponin C gene and the slow-twitch troponin I gene: hypozia-inducible nuclear factors [Semenza et al., *Proc. Natl. Acad. Sci. USA,* 88: 5680-5684 (1991)], steroid-inducible elements and promoters including the glucocorticoid response element (GRE) [See Mader and White, *Proc. Natl. Acad. Sci. USA,* 90: 5603-5607 (1993)], and other control elements.

DNA plasmids of the invention comprise rAAV genomes of the invention. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10 and AAV-11. Use of cognate components is specifically contemplated. Production of pseudotyped rAAV is disclosed in, for example, WO 01/83692 which is incorporated by reference herein in its entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988) and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. No. 5,786,211; U.S. Pat. No. 5,871,982; and U.S. Pat. No. 6,258,595. The foregoing documents are hereby incorporated by reference in their entirety herein, with particular emphasis on those sections of the documents relating to rAAV production.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

The rAAV may be purified by methods standard in the art such as by column chromatography or cesium chloride gradients. Methods for purifying rAAV vectors from helper virus are known in the art and include methods disclosed in, for example, Clark et al., Hum. Gene Ther., 10(6): 1031-1039 (1999); Schenpp and Clark, Methods Mol. Med., 69 427-443 (2002); U.S. Pat. No. 6,566,118 and WO 98/09657.

In another embodiment, the invention contemplates compositions comprising rAAV of the present invention. Compositions of the invention comprise rAAV in a pharmaceutically acceptable carrier. The compositions may also comprise other ingredients such as diluents. Acceptable carriers and diluents are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1 \times 10^6$, about $1 \times 10^7$, about $1 \times 10^8$, about $1 \times 10^9$, about $1 \times 10^{10}$, about $1 \times 10^{11}$, about $1 \times 10^{12}$, about $1 \times 10^{13}$ to about $1 \times 10^{14}$ or more DNase resistant particles (DRP) per ml. Dosages may also be expressed in units of viral genomes (vg) (i.e., $1 \times 10^7$ vg, $1 \times 10^8$ vg, $1 \times 10^9$ vg, $1 \times 10^{10}$ vg, $1 \times 10^{11}$ vg, $1 \times 10^{12}$ vg, $1 \times 10^{13}$ vg, $1 \times 10^{14}$ vg, respectively).

Methods of transducing a target cell (e.g., a skeletal muscle) with rAAV, in vivo or in vitro, are contemplated by the invention. The methods comprise the step of administering an effective dose, or effective multiple doses, of a composition comprising a rAAV of the invention to an animal (including a human being) in need thereof. If the dose is administered prior to development of DMD, the administration is prophylactic. If the dose is administered after the development of DMD, the administration is therapeutic. In embodiments of the invention, an effective dose is a dose that alleviates (eliminates or reduces) at least one symptom associated with DMD being treated, that slows or prevents progression to DMD, that slows or prevents progression of a disorder/disease state, that diminishes the extent of disease, that results in remission (partial or total) of disease, and/or that prolongs survival.

Administration of an effective dose of the compositions may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of rAAV (in particular, the AAV ITRs and capsid protein) of the invention may be chosen and/or matched by those skilled in the art taking into account the infection and/or disease state being treated and the target cells/tissue(s). In some embodiments, the route of administration is intramuscular. In some embodiments, the route of administration is intravenous.

Combination therapies are also contemplated by the invention. Combination as used herein includes simultaneous treatment or sequential treatments. Combinations of methods of the invention with standard medical treatments (e.g., corticosteroids and/or immunosuppressive drugs) are specifically contemplated, as are combinations with other therapies such as those mentioned in the Background section above.

BRIEF DESCRIPTION OF THE DRAWING

FIG. 9 shows the DNA sequence of the AAV genome insert (SEQ ID NO: 2) of the plasmid of FIG. 8.

EXAMPLES

Aspects and embodiments of the invention are illustrated by the following examples.

Example 1

Isolation of AAV rh.74

A unique AAV serotype was isolated from a rhesus macaque lymph node using a novel technique termed Linear Rolling Circle Amplification. Using the LRCA process, double-stranded circular AAV genomes were amplified from several rhesus macaques. The method is predicated on the ability to amplify circular AAV genomes by isothermic rolling circle amplification using phi29 phage DNA polymerase and AAV specific primers. LRCA products are contiguous head-to-tail arrays of the circular AAV genomes from which full-length AAV Rep-Cap molecular clones were isolated. Four isolates were sequenced and the predicted amino acid sequences for Rep and Cap ORFs were aligned and compared to previously published serotypes (Table). VP1 protein sequences were analyzed and revealed homology to the NHP AAV clades D, E, and AAV 4-like virus isolates. Analysis of the Rep78 (top portion of Table) ORF revealed strong homology to AAV 1 (98-99%).

TABLE 1

| | AAV 1 | AAV 4 | AAV 7 | AAV 8 | rh.73 | rh.74 | rh.75 | rh.76 |
|---|---|---|---|---|---|---|---|---|
| AAV 1 | | 90 | 98 | 95 | 98 | 98 | 99 | |
| AAV 4 | 63 | | 90 | 87 | 90 | 90 | 90 | |
| AAV 7 | 85 | 63 | | 96 | 97 | 98 | 98 | |
| AAV 8 | 84 | 63 | 88 | | 97 | 97 | 95 | |
| rh.73 | 79 | 61 | 83 | 80 | | 99 | 99 | |
| rh.74 | 84 | 63 | 88 | 93 | 80 | | 99 | |
| rh.75 | 65 | 82 | 82 | 64 | 62 | 64 | | |
| rh.76 | 85 | 63 | 91 | 86 | 84 | 86 | 84 | |

Similarity of published AAV sequences and the new AAV sequences determined using one-pair alignment according to the Lipman-Pearson method implemented in the MegAlgn software in DNASTAR (DNASTAR Inc.)
Light faced numbers (top, right) represent similarity in Rep78 sequences, whereas bold-faced numbers (lower, left) represent similarity in VP1 capsid sequences.

Figure 7A:
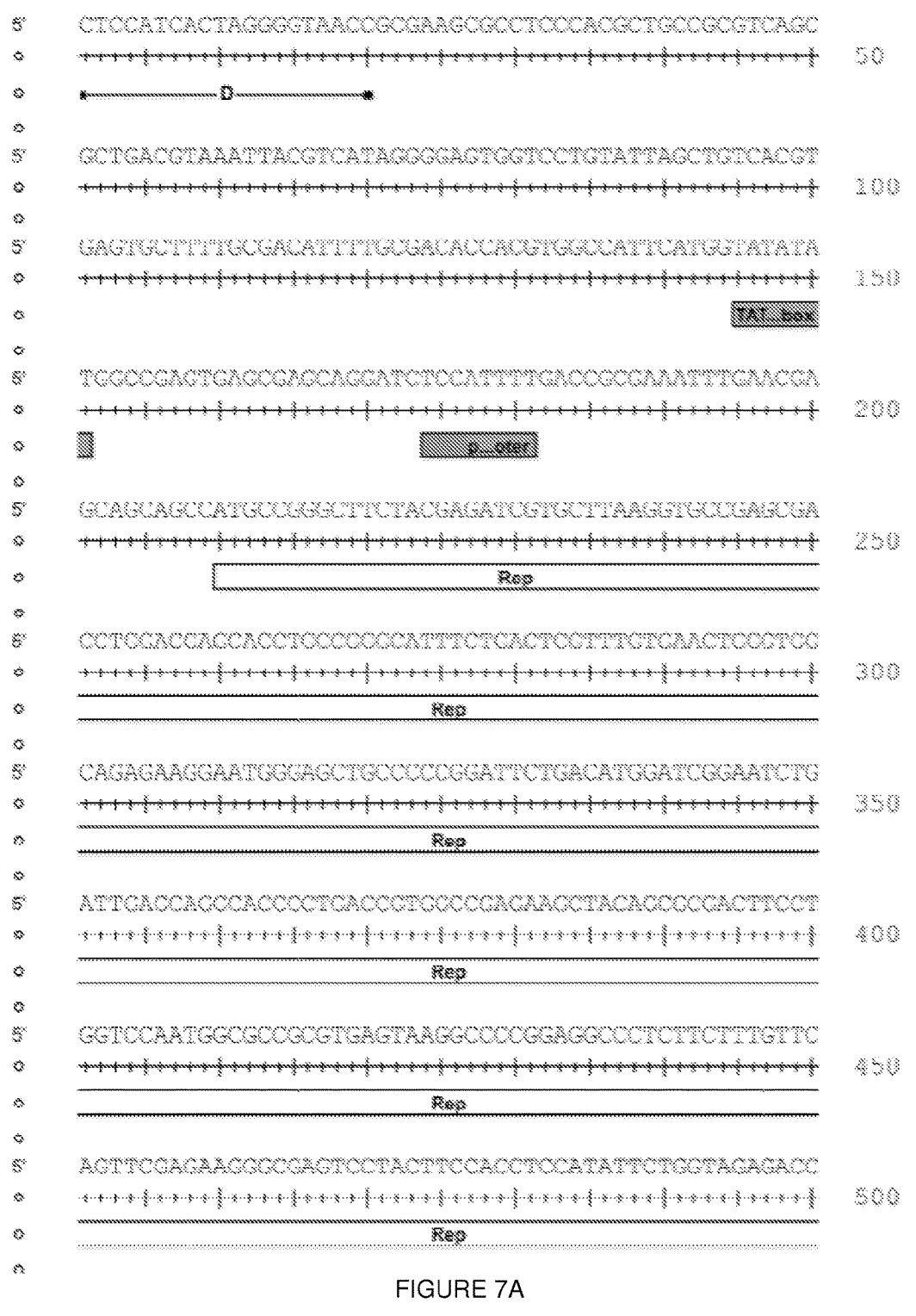
Figure 7E:
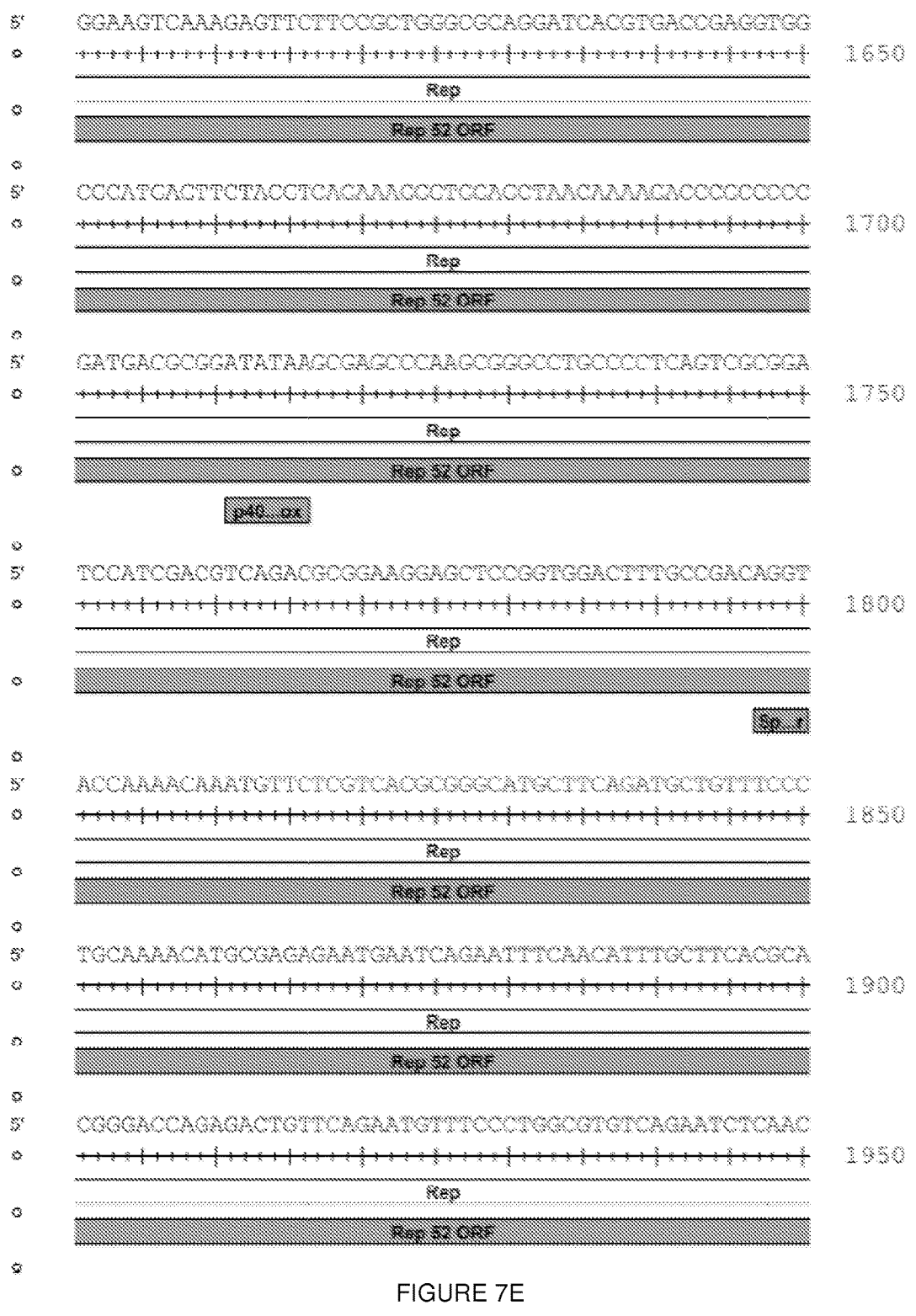
Figure 7F:
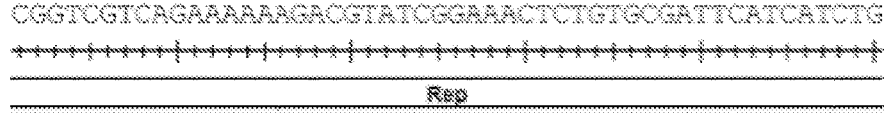
FIG. 7 is the rh74 genome sequence (SEQ ID NO: 1) wherein nucleotides 210-2147 are the Rep 78 gene open reading frame, 882-208 are the Rep52 open reading frame, 2079-2081 are the Rep78 stop, 2145-2147 are the Rep78 stop, 1797-1800 are a splice donor site, 2094-2097 are a splice acceptor site, 2121-2124 are a splice acceptor site, 174-181 are the p5 promoter +1 predicted, 145-151 are the p5 TATA box, 758-761 are the p19 promoter +1 predicted, 732-738 are the p19 TATA box, 1711-1716 are the p40 TATA box, 2098-4314 are the VP1 Cap gene open reading frame, 2509-2511 are the VP2 start, 2707-2709 are the VP3 start and 4328-4333 are a polyA signal.

One macaque tissue sample (rh426-M) yielded a divergent AAV8-like isolate termed rh.74 that shares 93% sequence identity with AAV8. The nucleotide sequence of the rh.74 genome is set out in FIG. 7 and in SEQ ID NO: 1.

The rh.74 capsid gene sequence was cloned into an AAV helper plasmid containing the Rep gene from AAV2 to provide vector replication functions for recombinant AAV vector production.

Example 2

DMD Models

Examples of models of the DMD exon 2 duplication include in vivo and in vitro models as follows.
mdx$^{dup2}$ Mouse Model Mice carrying a duplication of exon 2 within the Dmd locus were developed. The exon 2 duplication mutation is the most common human duplication mutation and results in relatively severe DMD.

Figure 10:
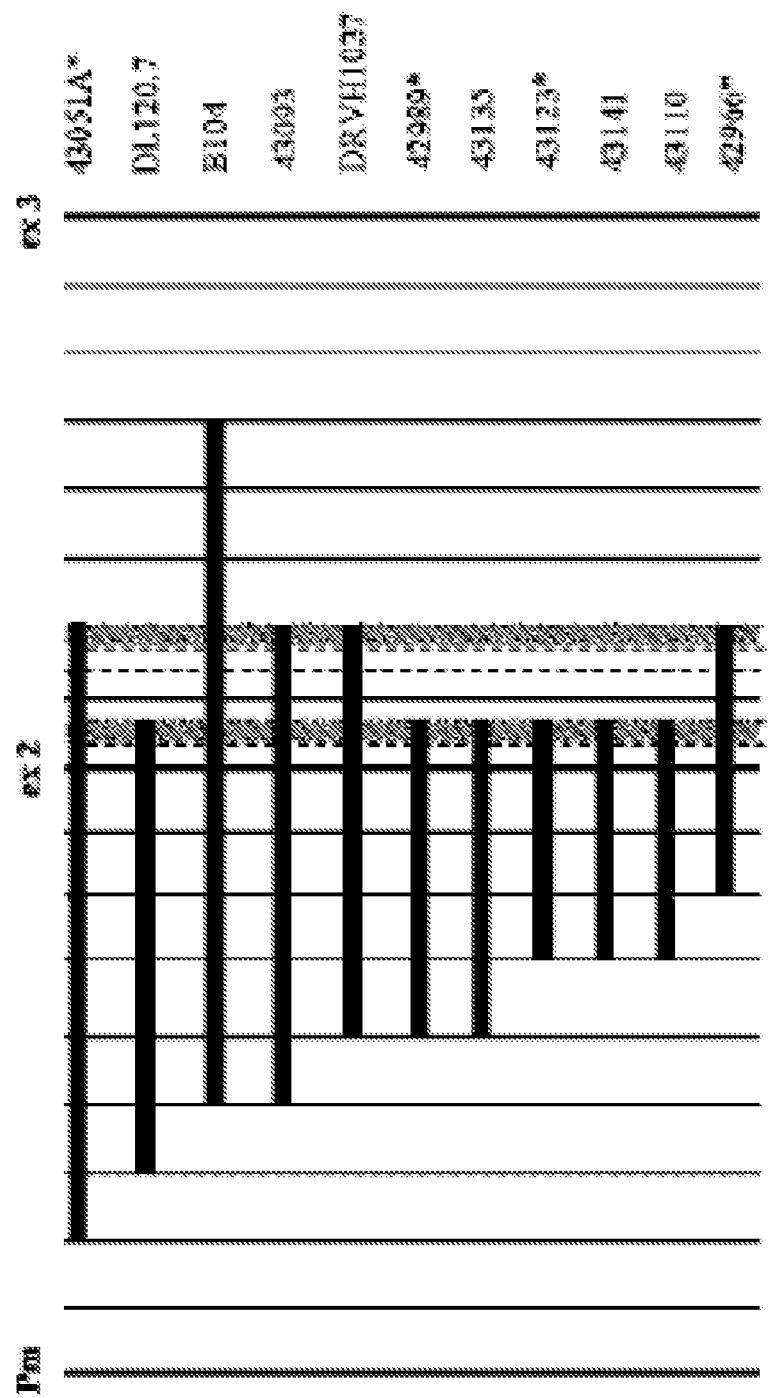
FIG. 10 shows vertical bars indicating the approximate position of an MLPA probe.

First, from White et al., Hum. Mutat., 27(9): 938-945 (2006), the maximum extent of the 11 different human exon 2 duplications was examined by MLPA and long-range PCR. Results are shown in FIG. 10. In FIG. 10, each vertical bar indicates the approximate position of an MLPA probe. The shaded columns indicate the two hotspot regions identified; they were used to determine the location of the insertion by homology of an exon 2 cassette in mouse.

Figure 11:
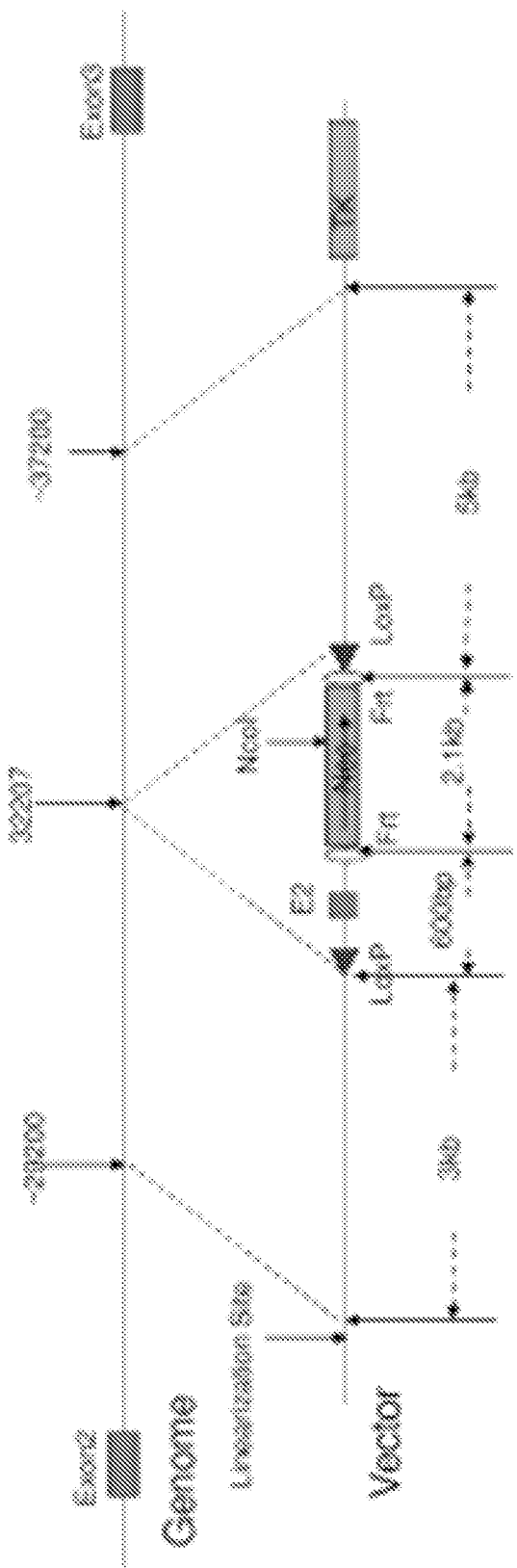
FIG. 11 shows a schematic of a vector used in creation of a mdx$^{dup2}$ (Dup2) mouse.

A map of the insertion vector is shown in FIG. 11. In the map, the numbers indicate the relative positions of cloning sites and exons and restriction sites. The neo cassette is in the same direction of the gene and the insertion point is precisely at 32207/32208 bp in the intron2. At least 150 bp extra intronic sequences are kept on each side of inserted exon 2, E2 region is 1775-2195 bp. Sizes of exon 2 and intron 2 are 62 bp and 209572 bp respectively.

Male C57BL/6 ES cells were transfected with the vector carrying the exon2 construct and then insertion was checked by PCR. One good clone was found, amplified and injected in dozens of albino BL/6 blastocysts. Injected blastocysts were implanted into recipient mice. The dystrophin gene from chimeric males was checked by PCR and then by RT-PCR. The colony was expanded and includes some female mice bred to homozygosity.

Figure 1:
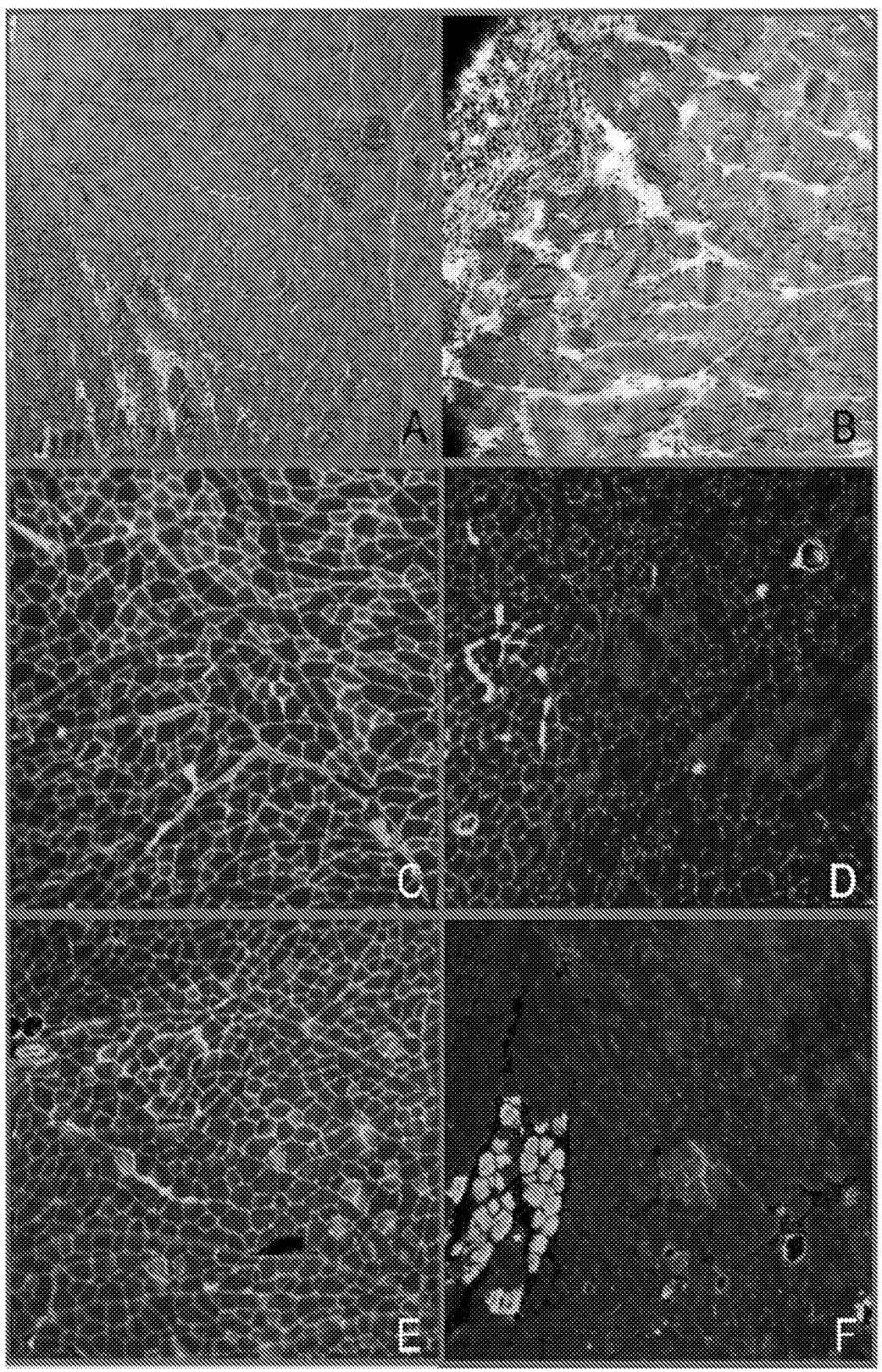
FIG. 1 shows histology and immunofluorescence analysis of muscles in the Dup2 mouse.
Figure 2:
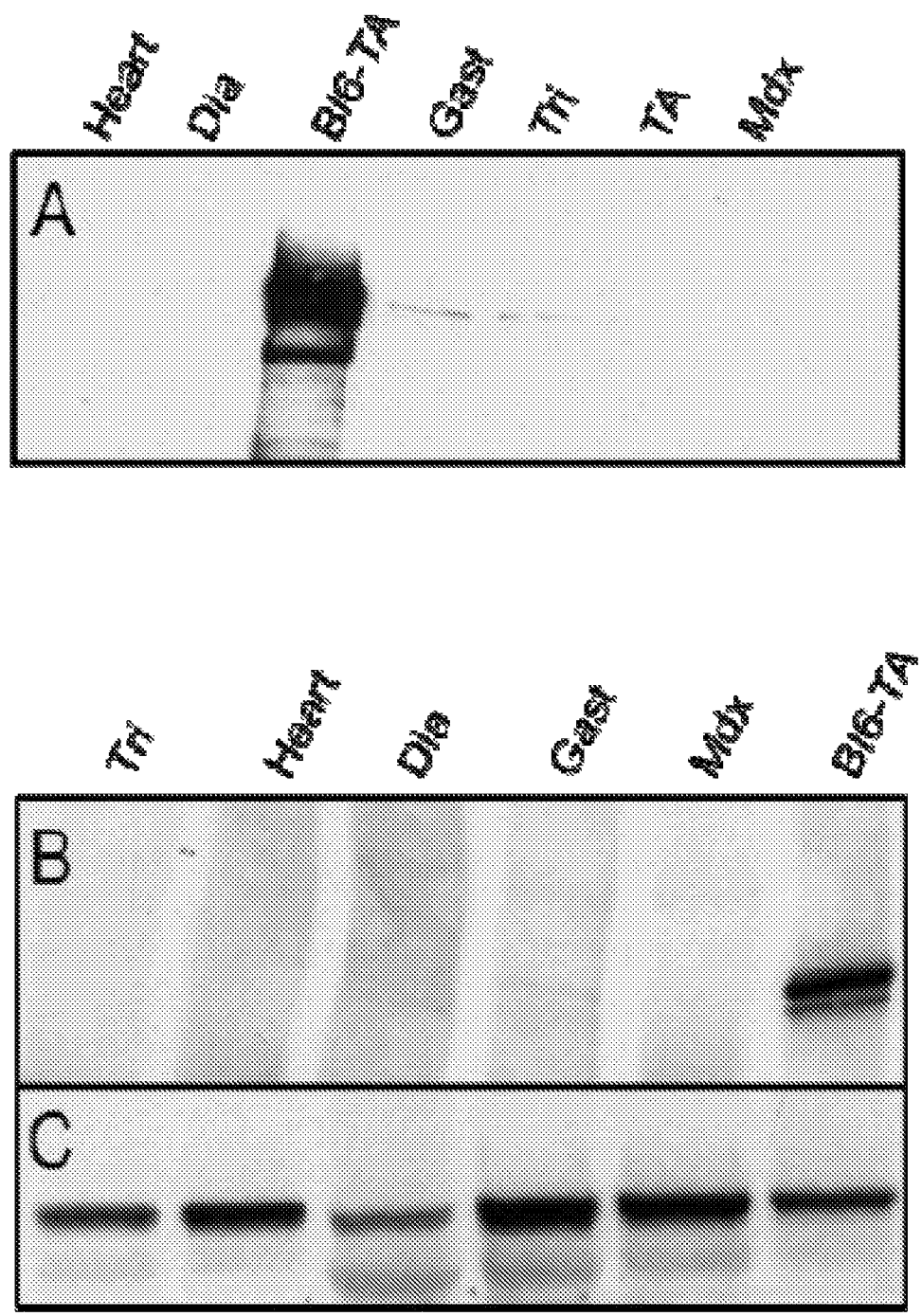
FIG. 2 shows immunoblots from Western blot analysis of muscles in the Dup 2 mouse.

FIG. 1 and FIG. 2 demonstrate the dystrophin expression in muscles from a 4 week old hemizygous mdxdup2 mouse is essentially absent. (As seen in FIG. 2, traces of expression can be detected using an C-terminal antibody but not the exon 1-specific Manex1A antibody, consistent with a very small amount of translation from the exon 6 alternate translational initiation site we previously described)

Immortalized and Conditionally Inducible fibroMyoD Cell Lines

Expression of the MyoD gene in mammalian fibroblasts results in transdifferentiation of cells into the myogenic lineage. Such cells can be further differentiated into myotubes, and they express muscle genes, including the DMD gene.

Immortalized cell lines that conditionally express MyoD under the control of a tetracycline-inducible promoter were generated. This is achieved by stable transfection of the primary fibroblast lines of a lentivirus the tet-inducible MyoD and containing the human telomerase gene (TER). The resultant stable line allows MyoD expression to be initiated by treatment with doxycycline. Such cell lines were generated from patients with DMD who carry a duplication of exon 2.

Figure 3:
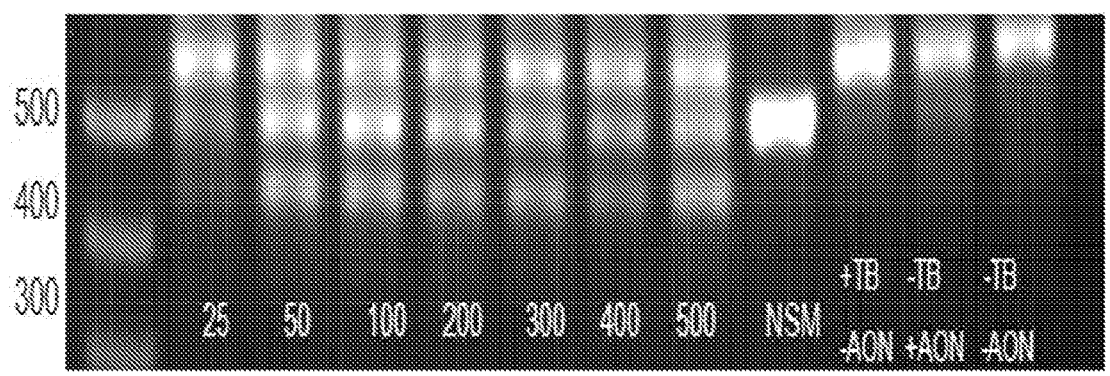
FIG. 3 shows skipping of a duplicated exon 2 in a MyoD-transdifferentiated myoblast induced by an AON directed at an exon splice enhancer results in 39% wild type transcript. Dosage per lane shown in nMoles (25, 50, 100, 200, 300, 400, 500). The amount of the varying transcripts are shown under each lane, with the maximum shaded. TB=transfection buffer. NSM=normal skeletal muscle. The percentage of exon 2 duplication, wt, and exon 2 deletion is listed below each lane.

Using the line, duplication skipping using 2'-O-methyl antisense oligomers (AONs) provided by Dr. Steve Wilton (Perth, Australia) was demonstrated. Multiple cell lines were tested. Results from exemplary cells lines are shown in FIG. 3.

Transiently MyoD-Transfected Primary Cell Lines

Proof-of-principle experiments using primary fibroblast lines transiently transfected with adenovirus-MyoD were conducted. The adenovirus constructs were not integrated in the cell genomes, yet MyoD was transiently expressed. The resulting DMD expression was sufficient to perform exon skipping experiments (although reproducibility favors the stably transfected lines.)

Example 3

Effectiveness of U7 snRNA-Mediated Skipping on Exon 2 Duplication Mutations

Products and methods for virally-mediated exon skipping of duplicated exons were developed. The products and methods were modified compared to the U7snRNA systems described in Goyenvalle et al., Science, 306(5702): 1796-1799 (2004) or Goyenvalle et al., Mol. Ther., 20(6): 179601799 (2004).

Figure 4:
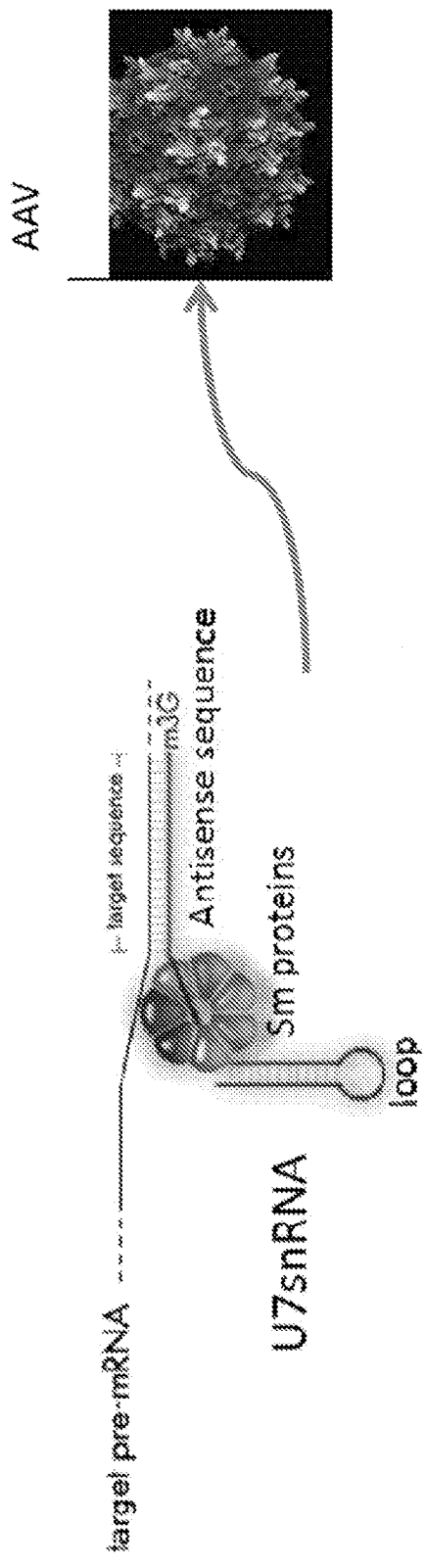
FIG. 4 illustrates the U7snRNA vector approach to exon skipping. U7snRNA is used as a carrier to target the pre-messenger RNA. It is composed of a loop used for the nucleocytoplasmic export, a recognition sequence to bind the Sm proteins used for an efficient assembly between the U7snRNA and the target pre-mRNA and an antisense sequence to target the pre-mRNA. It has its own promoter and 3' downstream sequences. The U7 cassette is then cloned in an AAV plasmid, to produce the vector.

U7snRNA was modified to include a target antisense sequence to interfere with splicing at a given target exon (FIG. 4). Specifically, four new exon 2 targeting sequences were designed based upon the results of the AON studies described in Example 2.

U7B
(SEQ ID NO: 3)
TCAAAAGAAAACATTCACAAAATGGGTA

-continued

U7Along
(SEQ ID NO: 4)
GTTTTCTTTTGAAGATCTTCTCTTTCATcta

U7Ashort
(SEQ ID NO: 5)
AGATCTTCTCTTTCATcta

U7C
(SEQ ID NO: 6)
GCACAATTTTCTAAGGTAAGAAT

U7 snRNA constructs including the exon 2 target sequences were generated. Each U7 snRNA construct included one of the target sequences. U7 snRNA constructs targeted to selected other exons were also generated (based upon MyoD-transdifferentiated cell line studies, above). Self complementary (SC) AAV vectors with genomes including one or more of the U7 snRNA constructs were then produced.

For experiments in cell culture and for intramuscular injection in Dup2 mice, rAAV1 vectors were utilized. Recombinant SC AAV vectors of a desired AAV serotype were produced by a modified cross-packaging approach using a plasmid comprising a desired vector genome by an adenovirus-free, triple plasmid DNA transfection (CaPO$_4$ precipitation) method in HEK293 cells [Rabinowitz et al., *J. Virol.*, 76:791-801 (2002)]. Vector was produced by co-transfecting with an AAV helper plasmid and an adenovirus helper plasmid in similar fashion as that previously described [Wang et al., *Gene. Ther.*, 10:1528-1534 (2003)]. The adenovirus helper plasmid (pAdhelper) expresses the adenovirus type 5 E2A, E4ORF6, and VA I/II RNA genes which are required for high-titer rAAV production.

Vectors were purified from clarified 293 cell lysates by sequential iodixanol gradient purification and anion-exchange column chromatography using a linear NaCl salt gradient as previously described [Clark et al., *Hum. Gene Ther*, 10:1031-1039 (1999)]. Vector genome (vg) titers were measured using QPCR based detection with a specific primer/probe set utilizing the Prism 7500 Taqman detector system (PE Applied Biosystems) as previously described (Clark et al., supra). Vector stock titers ranged between 1-10×10$^{12}$ vg/mL.

Initial exon-skipping analysis was by RT-PCR using the SC rAAV vectors to transduce Dup2 immortalized human fibromyoblasts. Dup 2 immortalized human fibroblasts that were able to transdifferentiate into muscle lineage cells under the control of doxycycline were produced by transduction with both telomerase-expressing and tet-inducible-MyoD expressing vectors. The converted human fibromyoblasts (FM) were then transduced with the SC rAAV carrying different U7 constructs incorporating exon 2 antisense sequences.

Figure 5:
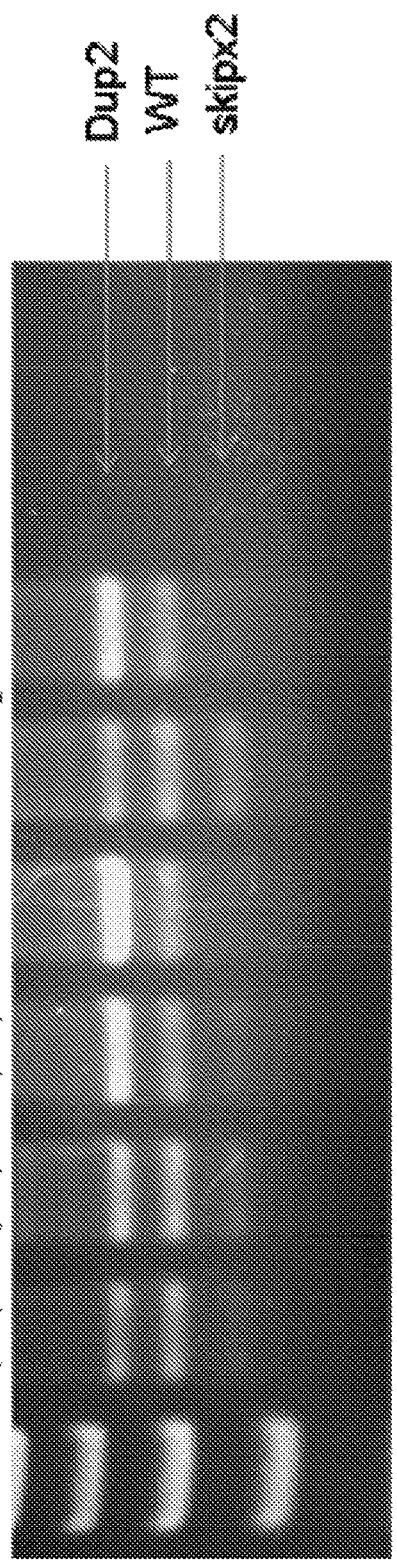
FIG. 5 shows RT-PCR results for exon-skipping experiments using SC rAAV vectors to transduce Dup2 immortalized human fibromyoblasts with exemplary exon 2-targeted U7snRNA constructs.
Figure 8:
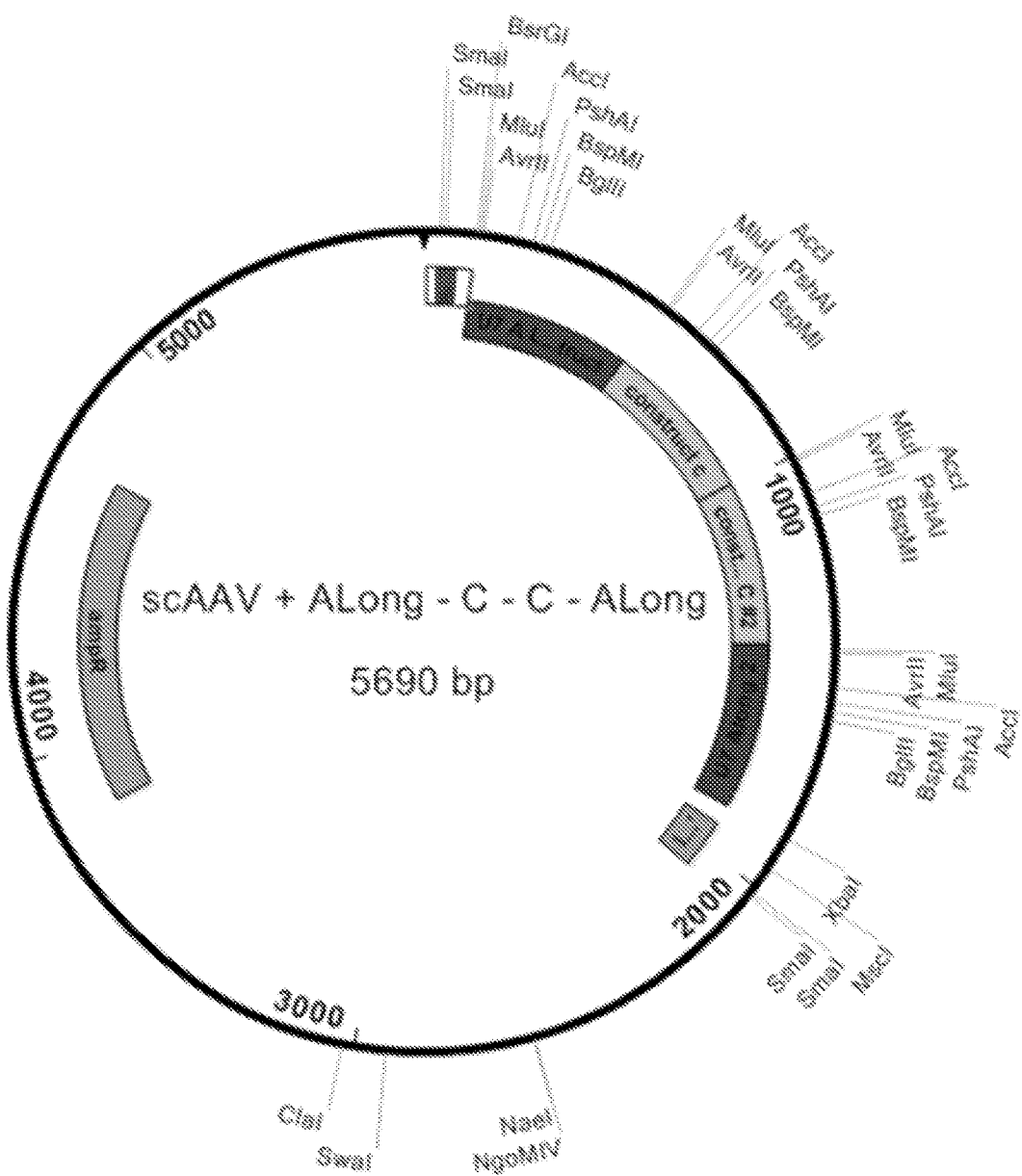
FIG. 8 shows a map of a plasmid with an AAV genome insert of an exemplary exon 2-targeted U7snRNA.

RT-PCR results are shown in FIG. 5 for SC rAAV.1-U7 constructs with three different antisense sequences. In FIG. 5, "(4C)" indicates four copies of the U7 construct were included in a vector genome, "+" indicates a higher dose and "U7_ACCA A=Along" indicates a vector genome (shown in a plasmid map in FIG. 8 and the sequence of which, SEQ ID NO: 2, is set out in FIG. 9) comprising in sequence four exon 2-targeted U7 snRNA polynucleotide constructs: a first U7Along construct, a first U7C construct, a second U7C construct and a second U7Along construct. As shown, the U7_ACCA A-Along SC rAAV (abbreviated U7_ACCA SC rAAV1 elsewhere herein) achieved a higher percentage of exon 2 skipping in comparison to any other vector construct.

Figure 6:
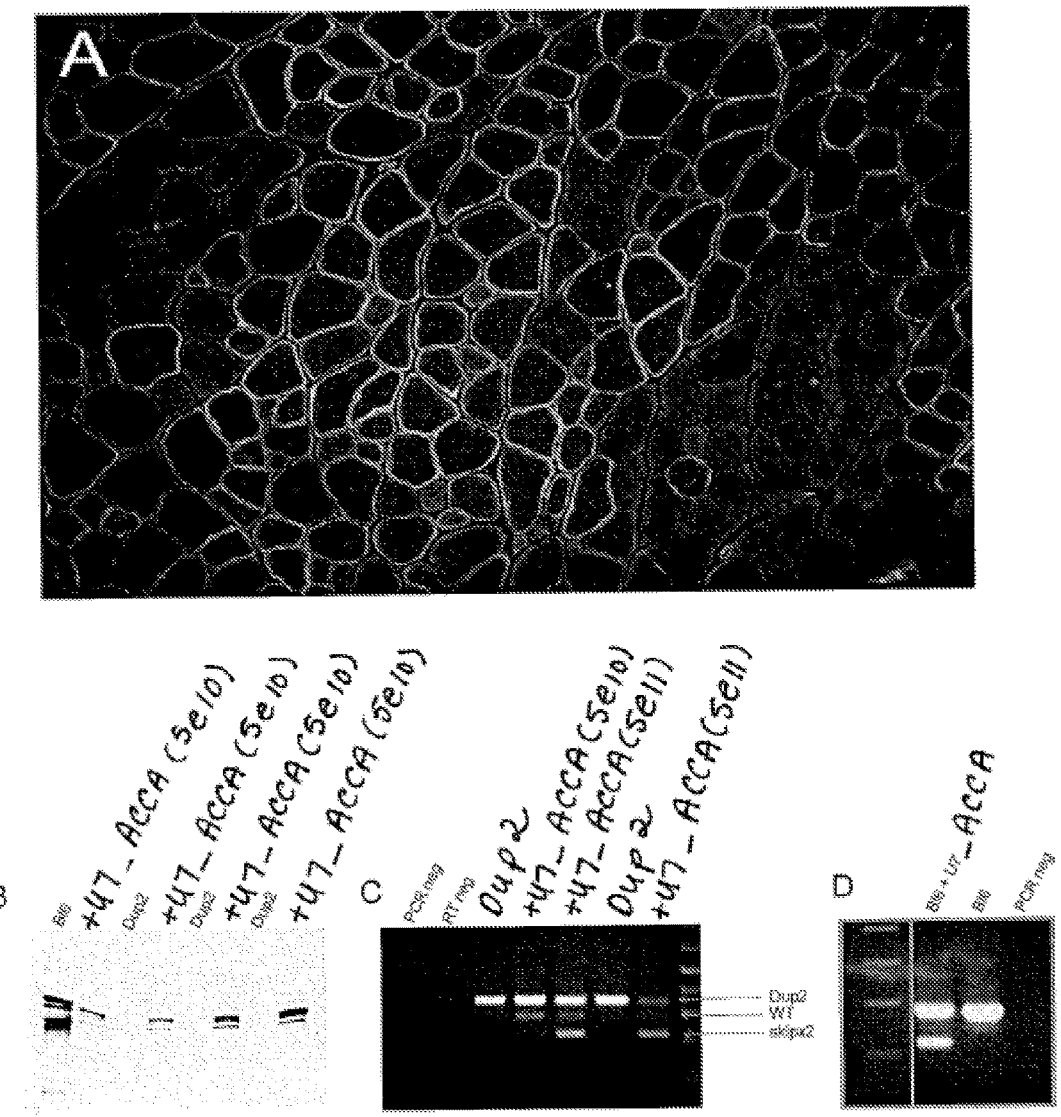
FIG. 6 (A-D) presents results for exon-skipping experiments in vivo in which U7_ACCA SC rAAV was delivered by intramuscular injection in Dup2 mice.

In subsequent experiments, exon-skipping efficiency was analyzed in vivo. The most efficient AAV-U7 vector, U7_ACCA SC rAAV1, was chosen for intramuscular injection in Dup2 mice. Results are shown below in FIG. 6 (A-D) wherein (A) shows dystrophin staining where the protein expression is restored, and is properly localized at the membrane in many muscle fibers; (B) protein restoration was confirmed by western blot. RT-PCR shows (C) dose-dependent single or double skipping in Dup2 mice, as well as (D) efficient skipping in the wild-type mouse.

Thus, a highly efficient AAV-mediated U7snRNA was designed to skip exon 2 allowing subsarcolemmal dystrophin restoration. Cardiac function; EDL and diaphragm force assessments; and treadmill and grip tests will be compared between untreated and treated mice.

Based upon the degree of dystrophin expression detectable within the injected muscle, U7_ACCA SC rAAV was chosen for further experiments to be delivered intraveneously to a first cohort at 1E11 vg/kg, followed by dosing one log higher in a second cohort. Injection will be performed at four weeks, and animals evaluated by physiologic assessment and histopathology at 10 and 24 weeks (n=8 animals per cohort) as described above.

Example 4

Intramuscular Delivery of U7-ACCA by AAV1 Results in Significant N-Truncated Dystrophin Expression in Dup2 Mice A rAAV1 comprising the genome insert of FIG. 9 was produced by the methods described in Example 3. The AAV.1U7-ACCA was then administered to Dup2 mice via intramuscular injection.

Figure 12:
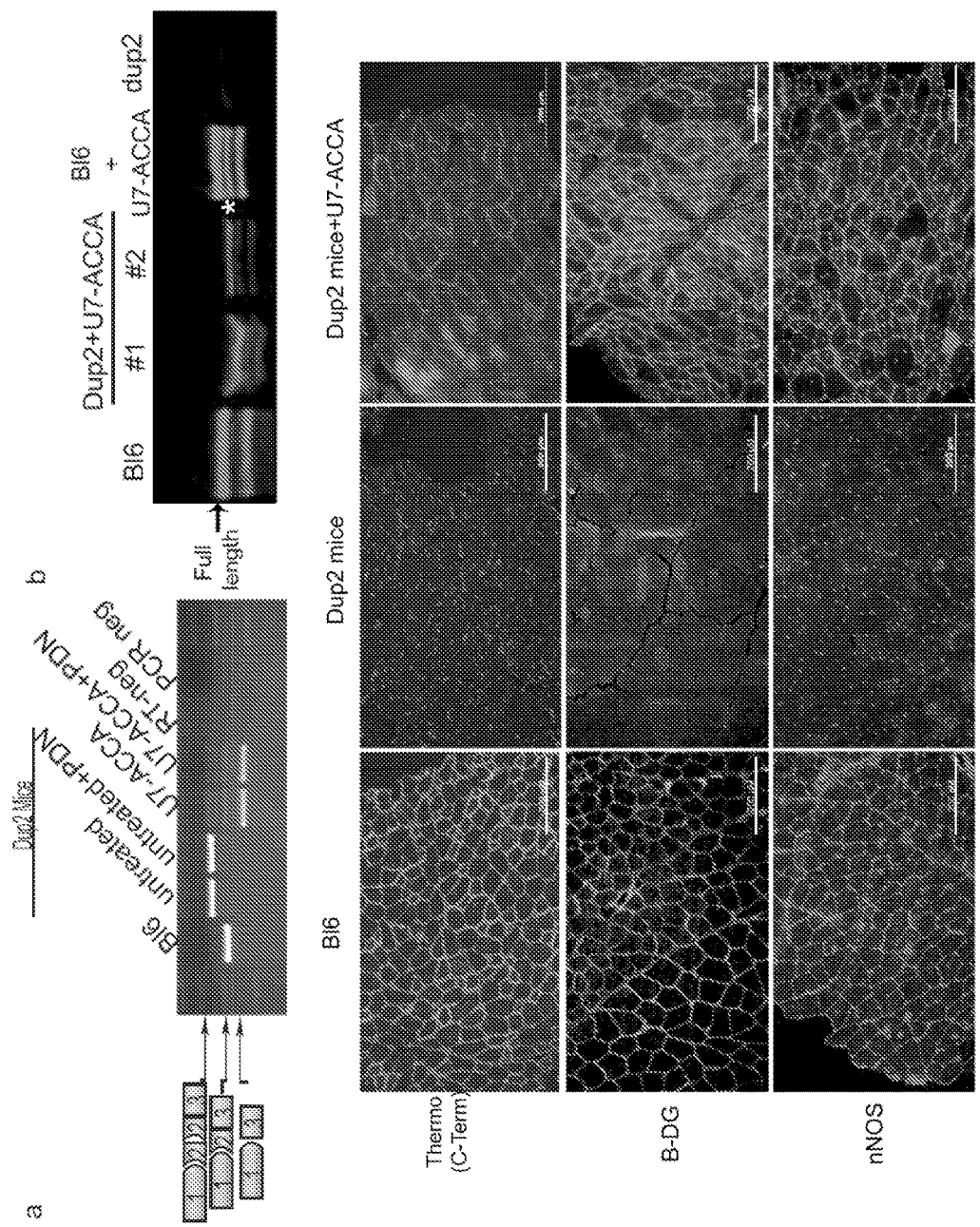
FIG. 12(a-e) shows the results of intramuscular delivery to Dup2 mice of AAV1 U7-ACCA.
Figure 12:
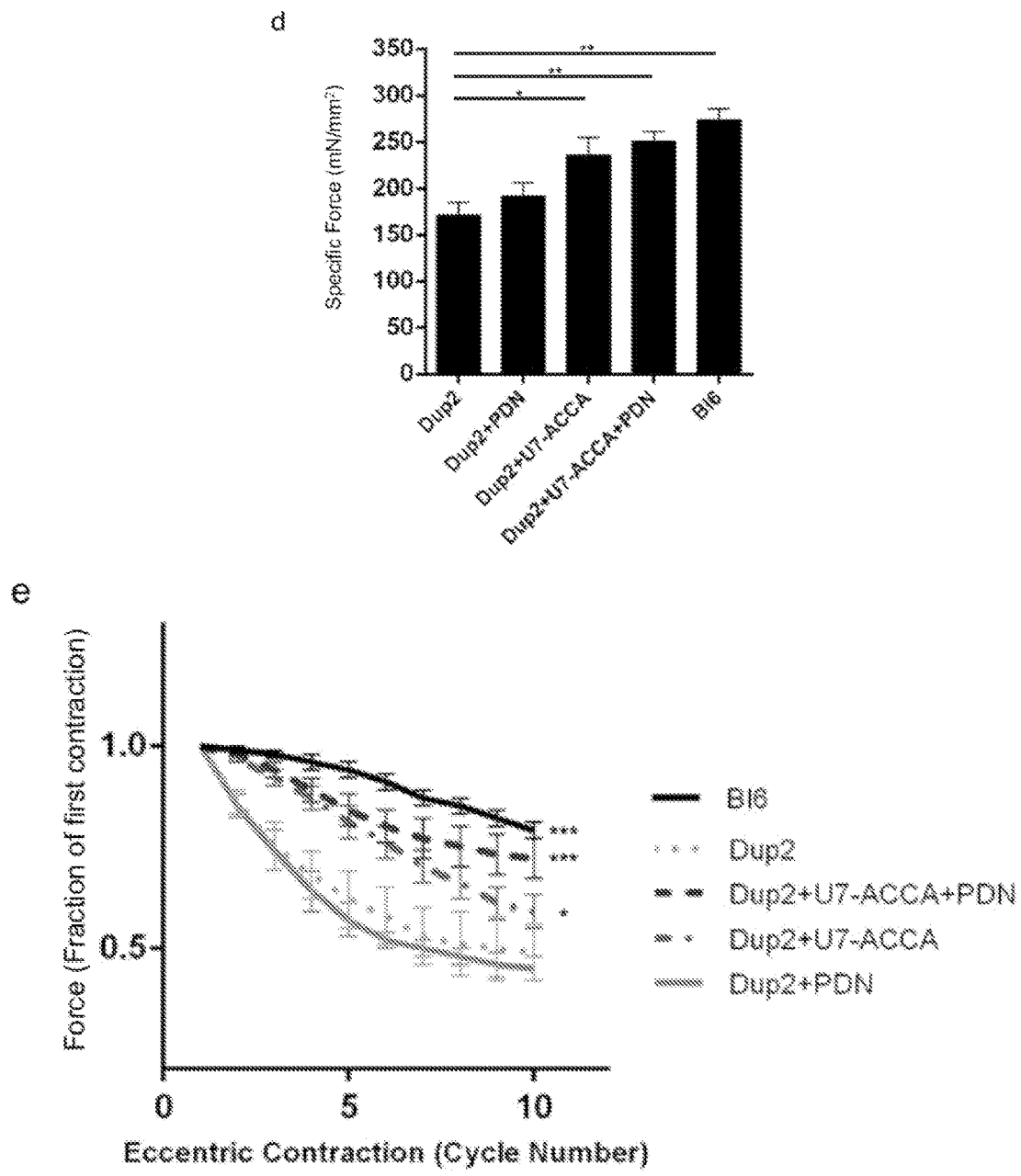

RT-PCR performed on DMD mRNA 4 weeks after TA intramuscular injection of 5e11vg AAV.1U7-ACCA showed nearly complete skipping of both copies of exon 2 in Dup2 animals [FIG. 12(*a*)].

Immunoblot using a C-terminal antibody (PA1-21011, ThermoScientific) performed a month after infection showed significant expression of the N-truncated isoform (asterisk) in both Dup2 and control Bl6 mice [FIG. 12(*b*)]. The protein induced in Bl6 males injected with U7-ACCA was of the same size as that expressed in the Dup2 treated animals, confirming the size difference between this protein and the full-length isoform.

Immunofluorescent staining of dystrophin, β-dystroglycan, and neuronal nitric oxide synthase demonstrated restoration of members of the dystrophin associated complex [FIG. 12(*c*)].

Normalized specific force following tetanic contraction in untreated Dup2 animals was significantly less than in Bl6 mice Intramuscular injection of AAV1.U7-ACCA, either alone or with prednisone, significantly increased force to levels that were not significantly different from that seen in Bl6 mice. No significant difference was observed between untreated Dup2 mice and those treated with prednisone along (Dup2+PDN) [FIG. 12(*d*)]. For this assay, normalized specific force was evaluated using a published protocol [Hakim et al., *Journal of Applied Physiology*, 110: 1656-1663 (2011)].

Treatment significantly protected Dup2 muscle from loss of force following repetitive eccentric contractions, as assessed by published protocols (Hakim et al., supra). Treatment of Dup2 mice with AAV1.U7-ACCA alone resulted in a statistically significant improvement compared to untreated Dup2 mice. The combination of AAV1.U7-ACCA and prednisone resulted in no significant difference in comparison to control Bl6 mice in force retention following contractions #3 to #10 [FIG. 12(e)].

Example 5

Intravenous Injection of AAV9-U7_ACCA in the Dup2 Mouse Model Results in Significant Expression of the N-Truncated Isoform and Correction of Strength Deficit Based upon the degree of dystrophin expression detectable within injected muscle, we chose to deliver U7_ACCA SC rAAV intraveneously for further experiments, and selected the serotype rAAV9 based upon known tissue distribution properties.

A rAAV9 comprising the genome insert of FIG. 9 was produced by the methods described in Example 3. The AAV.9U7-ACCA was then administered to Dup2 mice. A first cohort was injected via tail vein with 3.3E112 vg/kg. Injection was performed at four weeks of age.

Figure 13:
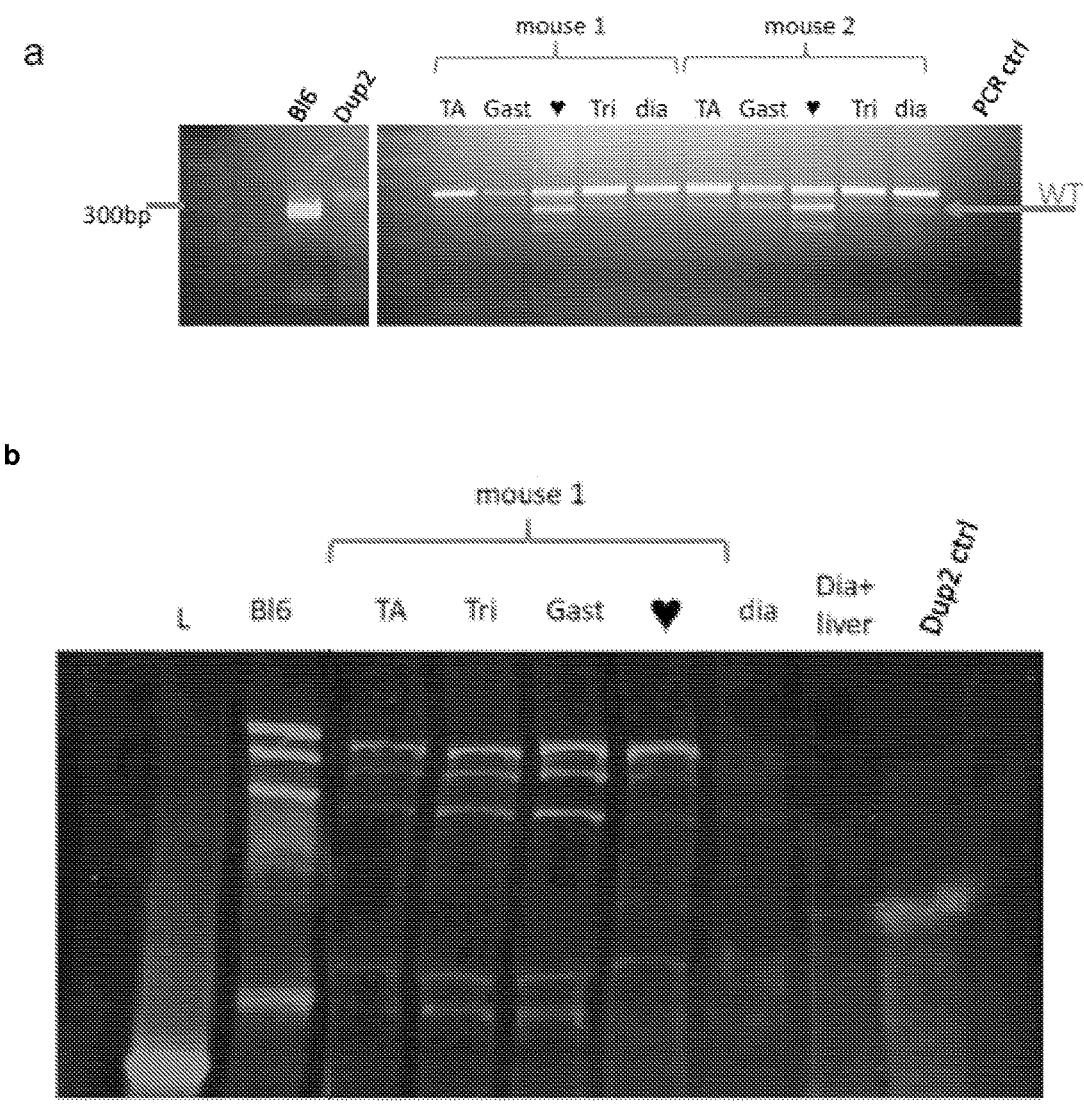
FIG. 13(a-f) shows the results of intravenous injection of AAV9 U7_ACCA in the Dup2 mouse model.
Figure 13:
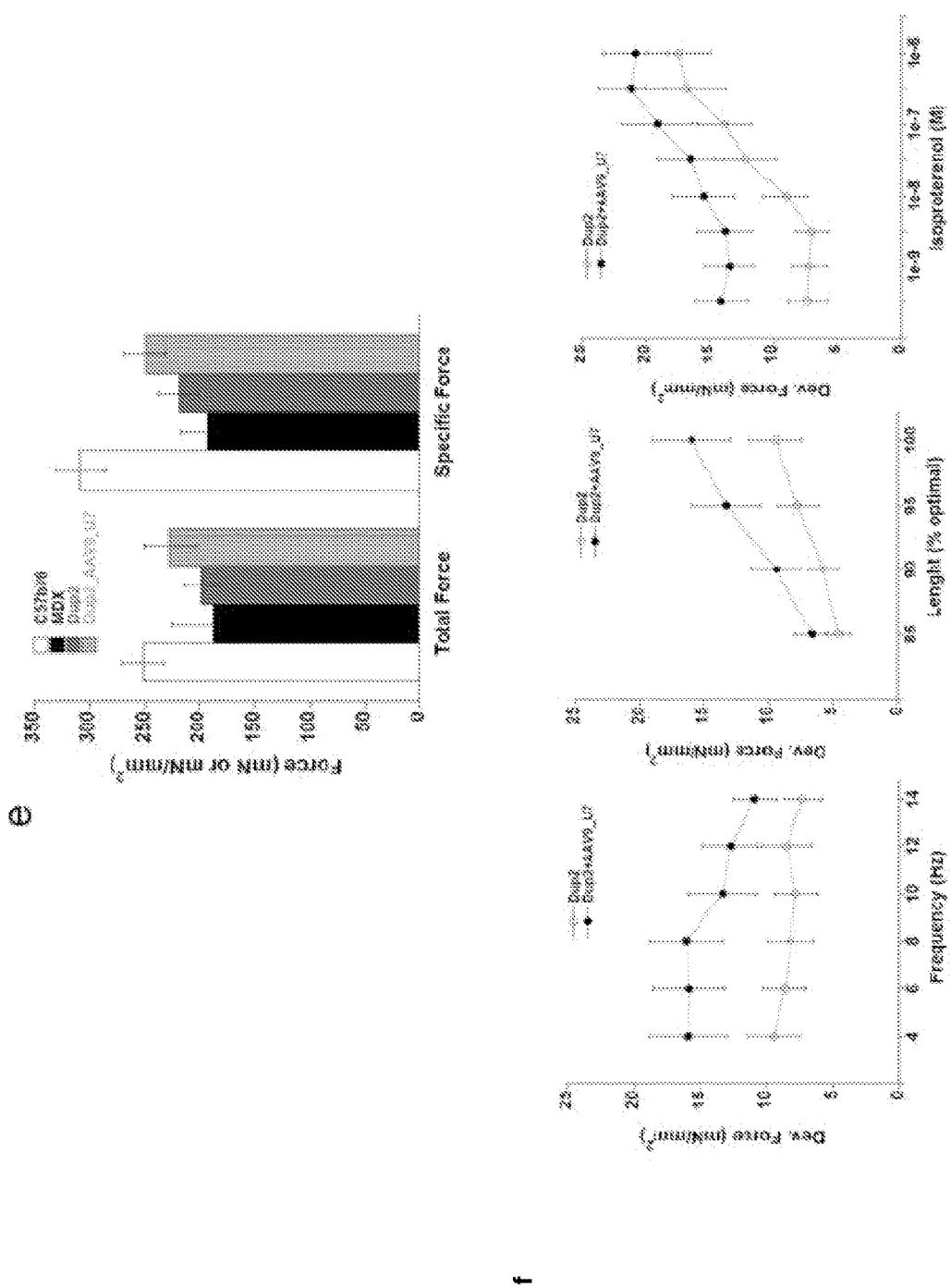

RT-PCR was performed on five different Dup2 mouse muscles one month after tail vein injection of AAV9.U7-ACCA (3.3E12 vg/kg) [FIG. 13(a)]. As demonstrated by the presence of multiple transcripts (labeled Dup2, wt, and De12), U7-ACCA treatment was able to force skipping of one or both copies of exon 2 in all muscles tested. (TA: tibialis anterior; Gas: gastrocnemius; ♥: heart; Tri: triceps; dia: diaphragm.)

Western blot using a C-terminal antibody (PA1-21011, ThermoScientific) performed on five different muscles one month after injection demonstrated the presence of dystrophin in all tested muscles[FIG. 13(b)].

Immunostaining using a C-terminal antibody (PA1-21011, ThermoScientific) of dystrophin on the same samples confirmed dystrophin expression and its proper localization at the sarcolemma [FIG. 13(c)].

Evaluation of both forelimb and hindlimb grip strength demonstrated a complete correction of grip strength in Dup2 animals treated with AAV9.U7-ACCA [FIG. 13(d)]. This assay was performed using a published protocol [Spurney, et al., *Muscle & Nerve*, 39, 591-602 (2009)].

Normalized specific and total forces following tetanic contraction showed improvement in muscle force in comparison to untreated Dup2 animals [FIG. 13(e)], using a published protocol [Hakim et al., supra).

Cardiac papillary muscles demonstrated improvements in length-dependent force generation in treated animals [FIG. 13(f)], using a published protocol [Janssen et al., *Am J Physiol Heart Circ Physiol.*, 289(6):H2373-2378 (2005)].

While the present invention has been described in terms of specific embodiments, it is understood that variations and modifications will occur to those skilled in the art. Accordingly, only such limitations as appear in the claims should be placed on the invention.

All documents referred to in this application are hereby incorporated by reference in their entirety with particular attention to the content for which they are referred.

We claim:

1. A method of ameliorating Duchenne Muscular Dystrophy in a patient with DMD exon 2 duplications in need thereof comprising the step of administering a recombinant adeno-associated virus (rAAV) to the patient, wherein the recombinant AAV comprises the genome insert set out in SEQ ID NO: 2.

2. A method of inhibiting the progression of dystrophic pathology associated with Duchenne Muscular Dystrophy in a patient with DMD exon 2 duplications in need thereof comprising the step of administering a rAAV to the patient, wherein the recombinant AAV comprises the genome insert set out in SEQ ID NO: 2.

3. A method of improving muscle function in a patient afflicted with Duchenne Muscular Dystrophy associated with DMD exon 2 duplications comprising the step of administering a rAAV to the patient, wherein the recombinant AAV comprises the genome insert set out in SEQ ID NO: 2.

4. The method of claim 3 wherein the improvement in muscle function is an improvement in muscle strength.

5. The method of claim 3 wherein the improvement in muscle function is an improvement in stability in standing and walking.

6. The method of any of claims 1-5 wherein the virus genome is a self-complementary genome.

7. A method of delivering an exon 2-targeted U7snRNA polynucleotide construct to an patient with DMD exon 2 duplications, comprising the step of administering a rAAV to the patient, wherein the recombinant AAV comprises the genome insert set out in SEQ ID NO: 2.

8. The method of claim 1, 2, 3, 4, 5 or 7 wherein genome of the rAAV lacks AAV rep and cap DNA.

9. The method of claim 7 wherein the virus genome is a self-complementary genome.

10. The method of claim 1, 2, 3, 4, 5 or 7 wherein the recombinant adeno-associated virus is a recombinant AAV rh74 virus, a recombinant AAV6 virus or a recombinant AAV9 virus.

11. A recombinant adeno-associated virus (AAV), wherein the recombinant AAV comprises the genome insert set out in SEQ ID NO: 2.

12. A recombinant adeno-associated virus (AAV) comprising an AAV rh.74 capsid, an AAV6 capsid or an AAV9 capsid; and the genome insert set out in SEQ ID NO: 2.

13. The rAAV of claim 11 or 12 wherein genome of the rAAV lacks AAV rep and cap DNA.

14. The rAAV of claim 11 or 12 wherein the genome is a self-complementary genome.

* * * * *